US009884821B2

(12) United States Patent
Min et al.

(10) Patent No.: US 9,884,821 B2
(45) Date of Patent: Feb. 6, 2018

(54) N1-CYCLIC AMINE-N5-SUBSTITUTED BIGUANIDE DERIVATIVES, METHODS OF PREPARING THE SAME AND PHARMACEUTICAL COMPOSITION COMPRISING THE SAME

(71) Applicant: IMMUNOMET THERAPEUTICS INC., Cambridge, MA (US)

(72) Inventors: Chang Hee Min, Seoul (KR); Yong Eun Kim, Daejeon (KR); Byung Kyu Oh, Chungcheongnam-do (KR); Ji Sun Lee, Daejeon (KR); Hye Jin Heo, Daejeon (KR); Ju Hoon Oh, Gangwon-do (KR); Woong Cho, Daejeon (KR)

(73) Assignee: ImmunoMet Therapeutics Inc., Houston, TX (US)

( * ) Notice: Subject to any disclaimer, the term of this patent is extended or adjusted under 35 U.S.C. 154(b) by 0 days.

(21) Appl. No.: 14/766,203

(22) PCT Filed: Feb. 6, 2014

(86) PCT No.: PCT/KR2014/001006
§ 371 (c)(1),
(2) Date: Aug. 6, 2015

(87) PCT Pub. No.: WO2014/123364
PCT Pub. Date: Aug. 14, 2014

(65) Prior Publication Data
US 2015/0368198 A1 Dec. 24, 2015

(30) Foreign Application Priority Data

Feb. 7, 2013 (KR) ........................ 10-2013-0014175
Feb. 7, 2013 (KR) ........................ 10-2013-0014176

(51) Int. Cl.
C07D 207/20 (2006.01)
C07D 211/14 (2006.01)
C07D 211/70 (2006.01)
C07D 211/16 (2006.01)

(52) U.S. Cl.
CPC .......... C07D 211/70 (2013.01); C07D 207/20 (2013.01); C07D 211/14 (2013.01); C07D 211/16 (2013.01)

(58) Field of Classification Search
CPC ... C07D 211/14; C07D 211/70; C07D 211/16; C07D 207/20
USPC ........................................................ 546/184
See application file for complete search history.

(56) References Cited

U.S. PATENT DOCUMENTS

| | | | |
|---|---|---|---|
| 2,467,371 A * | 4/1949 | Curd | C07C 279/26 546/231 |
| 3,960,949 A | 6/1976 | Ahrens et al. | |
| 7,622,117 B2 | 11/2009 | Tobia et al. | |
| 9,133,110 B2 * | 9/2015 | Kim | C07C 279/26 |
| 9,321,742 B2 * | 4/2016 | Kim | C07D 333/20 514/210.01 |
| 9,539,238 B2 * | 1/2017 | Kang | A61K 31/40 |
| 9,540,325 B2 * | 1/2017 | Kim | C07D 211/14 |
| 2012/0135952 A1 * | 5/2012 | Kim | A61K 31/155 514/49 |
| 2012/0283299 A1 * | 11/2012 | Kim | C07C 279/26 514/357 |
| 2012/0309799 A1 * | 12/2012 | Kim | C07C 279/26 514/357 |
| 2014/0179660 A1 * | 6/2014 | Kim | C07D 205/04 514/210.01 |
| 2014/0179661 A1 * | 6/2014 | Kim | C07D 333/20 514/210.01 |
| 2014/0235558 A1 * | 8/2014 | Kim | A61K 31/155 514/23 |
| 2014/0235559 A1 * | 8/2014 | Kim | A61K 31/7004 514/23 |
| 2015/0126518 A1 * | 5/2015 | Kim | C07D 495/04 514/252.12 |
| 2015/0376123 A1 * | 12/2015 | Kim | C07C 279/26 514/357 |
| 2016/0101112 A1 * | 4/2016 | Kim | A61K 31/155 514/210.01 |
| 2016/0317478 A1 * | 11/2016 | Kim | C07C 279/26 |

(Continued)

FOREIGN PATENT DOCUMENTS

| | | |
|---|---|---|
| GB | 599714 | 3/1948 |
| KR | 10-2013-0018622 | 2/2013 |
| KR | 10-2013-0019351 | 2/2013 |

(Continued)

OTHER PUBLICATIONS

Chemical Abstracts STN Registry Database record for RN 1092281-51-0 entered Dec. 31, 2008.*
Shapiro; Journal of the American Chemical Society, 1959, 81, 3728-3736.*
James; Journal of Medicinal Chemistry, 1968, 11, 942-945.*
Boggiano; Journal of Pharmacy and Pharmacology, 1961, 13, 567-574.*
Chemical Abstracts STN Registry Database records for RN 1349886-10-7 and RN 1347987-36-3, entered Dec. 6, 2011 and Dec. 4, 2011.*
Brzozowski; Acta Poloniae Pharmaceutica 36, 1979, 645-650.*
Curd; Journal of the Chemical Society 1946, 729-737.*
Rattan; Journal of Oncology 2012, Article ID 928127, 12 pages.*
Dowling; BMC Medicine 2011, 9-33.*

(Continued)

*Primary Examiner* — Daniel R Carcanague
(74) *Attorney, Agent, or Firm* — Clark & Elbing LLP

(57) ABSTRACT

The present invention provides an N1-cyclic amine-N5-substituted biguanide derivative compound represented by Formula 1, a method of preparing the same and a pharmaceutical composition including the biguanide derivative or the pharmaceutically acceptable salt thereof as an active ingredient. The biguanide derivatives have an effect of inhibiting cancer cell proliferation, cancer metastasis and cancer recurrence by activation of AMPK, even when administered in a small dose compared with conventional drugs.

12 Claims, No Drawings

(56) References Cited

U.S. PATENT DOCUMENTS

2016/0331724 A1\* 11/2016 Kang .................... A61K 31/402
2017/0073331 A1\* 3/2017 Kim ...................... C07C 279/04

FOREIGN PATENT DOCUMENTS

| KR | 10-2011-0081093 | | 6/2013 |
|----|----|----|----|
| WO | WO 92/07560 | | 5/1992 |
| WO | WO-2005079463 A2 | | 9/2005 |
| WO | WO 2013022278 | \* | 2/2013 |
| WO | WO 2013022279 | \* | 2/2013 |
| WO | WO 2013188452 | \* | 12/2013 |
| WO | WO2016080810 | \* | 5/2016 |

OTHER PUBLICATIONS

Russo; Biochemical Pharmacology 2013, 86, 339-350.\*

Extended European search report for application 14748929.8, dated Sep. 28, 2016, 9 pages.
Boutet et al., "Snail activation disrupts tissue homeostasis and induces fibrosis in the adult kidney," EMBO J. 25(23):5603-13 (2006).
Derynck et al., "Differentiation plasticity regulated by TGF-beta family proteins in development and disease," Nat Cell Biol. 9(9):1000-4 (2007).
Hutchison et al., "Resident mesenchymal cells and fibrosis," available in PMC Jul. 1, 2014, published in final edited form as: Biochim Biophys Acta. 1832(7):962-71 (2013) (21 pages).
International Search Report for International Application No. PCT/KR2014/004474, dated Aug. 7, 2014 (6 pages).
Tak, "Investigation of the Antifibrotic Effect of Erythropoietin (EPO) from Hepatic Cirrhosis Animal model," Clin Mol Hepatol. 13(4S);S74-8 (2007).
Willis et al., "TGF-beta-induced EMT: mechanisms and implications for fibrotic lung disease," Am J Physiol Lung Cell Mol Physiol. 293(3):L525-34 (2007).

\* cited by examiner

N1-CYCLIC AMINE-N5-SUBSTITUTED BIGUANIDE DERIVATIVES, METHODS OF PREPARING THE SAME AND PHARMACEUTICAL COMPOSITION COMPRISING THE SAME

RELATED APPLICATIONS

This application is a 35 U.S.C. § 371 national phase application of PCT/KR2014/001006 (W02014/123364), filed on Feb. 6, 2014, entitled "N1-Cyclic Amine-N5-Substituted Biguanide Derivatives, Methods of Preparing the Same and Pharmaceutical Composition Comprising the Same", which application claims priority to and the benefit of Korean Patent Application No. 10-2013-0014175, filed Feb. 7, 2013 and Korean Patent Application No. 10-2013-0014176, filed Feb. 7, 2013, the disclosures of which are incorporated herein by reference in their entirety.

TECHNICAL FIELD

The present invention relates to an N1-cyclic amine-N5-substituted biguanide derivative that inhibits cancer cell proliferation, cancer metastasis and cancer recurrence by activation of AMPK, even when administered in a small dose compared with conventional drugs, and that exhibits excellent therapeutic effects, a method of preparing the same, and a pharmaceutical composition including the N1-cyclic amine-N5-substituted biguanide derivative as an active ingredient.

BACKGROUND ART

AMPK (AMP-activated protein kinases) is an enzyme that functions to regulate a metabolic pathway so as to maintain balance between supply of nutrients and demand for energy, and thus maintain energy homeostasis in cells and the whole body. AMPK is activated as a ratio of AMP/ATP in the cells increases due to a hypoxemic state or glucose deficiency. The activated AMPK induces fatty acid oxidation to produce a larger amount of ATP and inhibits anabolisms requiring the use of ATP. AMPK inhibits proliferation of cancer cells and kills the cancer cells by regulating energy metabolism in the cancer cells as well as in normal cells. AMPK activated in the cancer cells shows anticancer activities by phosphorylating mTORC1, p53, fatty acid synthase and the like to regulate the cell cycle, cell polarity, autophagy, apoptosis, etc.

Metformin has been used to treat insulin-independent diabetes mellitus (i.e., type II diabetes mellitus) since, among oral therapeutic agents for treating diabetes mellitus, it is most effective at lowering blood glucose, does not cause hypoglycemia or hyperinsulinemia and can prevent complications. In recent years, metformin has been extensively researched. Also, it was reported that metformin activates AMP-activated protein kinase (AMPK) by inhibiting the action of complex 1 of the electron transport system in mitochondria to obstruct intracellular generation of energy, and inhibits activation of the mTOR/S6K1 signaling pathway in which proteins essential for survival are produced to obstruct proliferation of cancer cells and tumor growth (Mol. Cancer Ther. 9(5): 1092-1099 (2010)). Consequently, metformin has received considerable attention as an anticancer agent for regulating cancer cell metabolism. Also, an epidemiological survey confirmed that the incidence of cancer and mortality by cancer were lower for patients treated with metformin (BMJ.330: 1304-1305 (2005)).

Meanwhile, there is increasing clinical evidence indicating that cancer stem cells take part in recurrence and metastasis of cancer. The cancer stem cells refer to cancer cells that have self-regeneration or differentiation activities which are characteristically innate to stem cells. The cancer stem cells are present in the cancer tissues at a content of 0.2% or less, and are characterized by their slow proliferation. Since many anticancer agents developed so far target cancer cells that proliferate rapidly, the cancer stem cells are resistant to conventional anticancer therapy when cancer stem cells are treated with the anticancer agents, thereby causing poor prognoses. On the other hand, it was reported that metformin prevents the recurrence of cancer as it selectively acts only on cancer stem cells among breast cancer cells and removes the cancer stem cells (Cancer Res. 69(19): 7507-11 (2009)). Also, it was found that metformin prevents the metastasis of cancer by interfering with the motility and invasion of the cancer since it inhibits the expression of Snail1, Slug, Twist, ZEB1/2 and TGF-b, which are transcription factors associated with the epithelial-to-mesenchymal transition (EMT) and promotes the expression of E-cadherin to prevent cancer cells from leading to the EMT (Cell Cycle 10: 7, 1144-1151 (2011), Cell Cycle 9: 18, 3807-3814 (2010), Cell Cycle 9: 22, 4461-4468 (2010)).

For these reasons, there is need for a biguanide-based substance that exhibits better pharmacological action than conventional metformin and has improved physiochemical properties.

DISCLOSURE OF INVENTION

Technical Problem

The present invention is directed to providing a novel biguanide derivative that is highly effective at inhibiting proliferation of cancer cells, cancer metastasis and cancer recurrence, even when administered in a small dose compared with conventional drugs, or a pharmaceutically acceptable salt thereof, and a method of preparing the same.

Solution to Problem

One aspect of the present invention provides an N1-cyclic amine-N5-substituted biguanide derivative compound represented by the following Formula 1, or a pharmaceutically acceptable salt thereof:

[Formula 1]

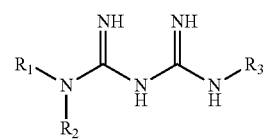

In Formula 1, $R_1$ and $R_2$ are taken together with nitrogen to which they are attached to form $C_{3-6}$ heterocycloalkene having 4 to 7 ring atoms; or $C_{3-6}$ heterocycloalkyl having 4 to 7 ring atoms, and $R_3$ is hydrogen; $C_{1-6}$ alkyl; phenyl; or $C_{1-4}$ alkyl substituted with phenyl, wherein the $C_{3-6}$ heterocycloalkene and the $C_{3-6}$ heterocycloalkyl are each independently unsubstituted or substituted with at least one substituent selected from the group consisting of halogen, hydroxy and $C_{1-6}$ alkyl, and the phenyl is unsubstituted or substituted with at least one non-hydrogen substituent selected from the group consisting of halogen, hydroxy, $C_{1-6}$ alkyl, $C_{1-6}$ alkoxy, $C_{1-6}$ haloalkyl, and $C_{1-6}$ haloalkoxy.

In this specification, a substituted group refers to a group in which at least one hydrogen atom is replaced with at least one non-hydrogen atom group, provided that the group satisfies the valence electron requirements and forms a chemically stable compound from the substitution. Unless explicitly described as unsubstituted in this specification, it should be understood that all substituents will be unsubstituted or substituted with another substituent. The substituents $R_1$ to $R_3$ on the biguanide derivative according to the present invention may each be re-substituted with at least one of the above-defined substituents.

The term halogen or halo- refers to fluoro, chloro, bromo, and iodo.

The term hydroxy refers to —OH.

The term alkyl refers to a linear and branched saturated hydrocarbon group generally having a specified number of carbon atoms (for example, 1 to 12 carbon atoms). Examples of the alkyl group include, without limitation, methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl, and n-octyl, etc. The alkyl may be attached to a parent group or a substrate at any ring atom, unless the attachment would violate the valence electron requirements. Likewise, the alkyl group may include at least one non-hydrogen substituent unless the substitution would violate the valence electron requirements. For example, the term haloalkyl refers to an alkyl group in which at least one hydrogen atom of the alkyl group is substituted with halogen. For example, when at least one hydrogen atom of methyl group is substituted with halogen, group such as —$CH_2$(halo), —CH(halo)$_2$ or C(halo)$_3$ is formed. Examples of the term haloalkyl group include, without limitation, trifluoromethyl, trichloromethyl, tribromomethyl, and triiodomethyl.

The term alkoxy refers to alkyl-O—, provided that the alkyl is the same as defined above. Examples of the alkoxy group include, without limitation, methoxy, ethoxy, n-propoxy, i-propoxy, n-butoxy, s-butoxy, t-butoxy, n-pentoxy, s-pentoxy, etc. The alkoxy may be attached to a parent group or a substrate at any ring atom, unless the attachment would violate the valence electron requirements. Likewise, the alkoxy group may include at least one non-hydrogen substituent unless the attachment would violate the valence electron requirements. For example, the term haloalkoxy refers to an alkoxy group in which at least one hydrogen atom of the alkoxy group is substituted with halogen. For example, when at least one hydrogen atom of methoxy group is substituted with halogen, group such as —O—$CH_2$(halo), —O—CH(halo)$_2$ or —O—C(halo)$_3$ is formed. Examples of the term haloalkoxy group include, without limitation, trifluoromethoxy, trichloromethoxy, tribromomethoxy, and triiodomethoxy, etc.

The term cycloalkene refers to a saturated monocyclic and polycyclic hydrocarbon ring generally having the specified number of carbon atoms (for example, $C_{3-8}$ cycloalkene refers to cycloalkene group having 3, 4, 5, 6, 7 or 8 carbon atoms as ring members). The cycloalkene may be attached to a parent or substrate at any ring atom, unless the attachment would violate the valence electron requirements. Likewise, the cycloalkene group may include at least one non-hydrogen substituent unless the substitution would violate the valence electron requirements.

The term heterocycloalkene refers to an unsaturated non-aromatic monocyclic and polycyclic hydrocarbon ring in which at least one of ring members in the cycloalkene is composed of elements rather than carbon, including heteroatoms, for example, nitrogen, oxygen or sulfur. The heterocycloalkene may be attached to a parent or substrate at any ring atom, unless the attachment would violate the valence electron requirements. Likewise, the heterocycloalkene group may include at least one non-hydrogen substituent unless the attachment would violate the valence electron requirements. Examples of the heterocycloalkene group include, without limitation, dihydroazetine, dihydropyrrole, dihydropyridine, tetrahydropyridine, dihydroazepine, tetrahydroazepine, etc.

The term cycloalkyl refers to a saturated monocyclic and dicyclic hydrocarbon ring generally having the specified number of carbon atoms included in a ring (that is, $C_{3-8}$ cycloalkyl refers to cycloalkyl group having 3, 4, 5, 6, 7 or 8 carbon atoms as ring members). The cycloalkyl may be attached to a parent or substrate at any ring atom, unless the attachment would violate the valence electron requirements. Likewise, the cycloalkyl group may include at least one non-hydrogen substituent unless the substitution would violate the valence electron requirements.

The term heterocycloalkyl refers to a monocyclic and dicyclic hydrocarbon ring in which at least one of ring system atoms in the cycloalkyl is composed of elements rather than carbon, including heteroatoms, that is, nitrogen, oxygen or sulfur. The heterocycloalkyl may be attached to a parent or substrate at any ring atom, unless the attachment would violate the valence electron requirements. Likewise, the heterocycloalkyl group may include at least one non-hydrogen substituent unless the substitution would violate valence electron requirements. Examples of the heterocycloalkyl group include, without limitation, aziridine, azetidine, imidazolyl, pyrrolyl, pyrrolidinyl, piperidyl, morpholinyl, piperazinyl, azepanyl, indolyl, indolinyl, etc.

According to one exemplary embodiment, $R_1$ and $R_2$ may be taken together with nitrogen to which they are attached to form $C_{4-5}$ heterocycloalkene having 5 to 6 ring atoms or $C_{4-5}$ heterocycloalkyl having 5 to 6 ring atoms, and $R_3$ may be hydrogen; $C_{1-6}$ alkyl; phenyl; or $C_{1-4}$ alkyl substituted with a phenyl, wherein the $C_{4-5}$ heterocycloalkene is unsubstituted or substituted with $C_{1-6}$ alkyl, the $C_{4-5}$ heterocycloalkyl is substituted with 1 to 4 $C_{1-6}$ alkyl groups, and the phenyl is unsubstituted or substituted with at least one non-hydrogen substituent selected from the group consisting of halogen, hydroxy, $C_{1-6}$ alkyl, $C_{1-6}$ alkoxy, $C_{1-6}$ haloalkyl, and $C_{1-6}$ haloalkoxy.

According to another exemplary embodiment, $R_1$ and $R_2$ may be taken together with nitrogen to which they are attached to form $C_{4-5}$ heterocycloalkene having 5 to 6 ring atoms or $C_{4-5}$ heterocycloalkyl having 5 to 6 ring atoms, $R_3$ may be hydrogen; $C_{1-6}$ alkyl; phenyl; or $C_{1-2}$ alkyl substituted with phenyl, wherein the $C_{4-5}$ heterocycloalkene is unsubstituted or substituted with $C_{1-2}$ alkyl, the $C_{4-5}$ heterocycloalkyl is substituted with one or two $C_{1-2}$ alkyl groups, and the phenyl is unsubstituted or substituted with at least one non-hydrogen substituent selected from the group consisting of halogen, $C_{1-2}$ alkoxy, $C_{1-2}$ haloalkyl, and $C_{1-2}$ haloalkoxy.

According to still another exemplary embodiment, $R_1$ and $R_2$ may be taken together with nitrogen to which they are attached to form $C_{3-6}$ heterocycloalkene selected from the group consisting of dihydroazetinyl; dihydropyrrolinyl; dihydropyridinyl; and tetrahydropyridinyl, or $R_1$ and $R_2$ may be taken together with nitrogen to which they are attached to form $C_{3-6}$ heterocycloalkyl selected from the group consisting of azetidinyl; piperidinyl; and pyrrolidinyl, and $R_3$ may be hydrogen; $C_{1-6}$ alkyl; phenyl; or $C_{1-4}$ alkyl substituted with phenyl, wherein the $C_{3-6}$ heterocycloalkene is unsubstituted or substituted with $C_{1-6}$ alkyl, the $C_{3-6}$ heterocycloalkyl is substituted with 1 to 4 $C_{1-6}$ alkyl groups, and the phenyl is unsubstituted or substituted with at least one non-hydrogen substituent selected from the group consisting of halogen, hydroxy, $C_{1-6}$ alkyl, $C_{1-6}$ alkoxy, $C_{1-6}$ haloalkyl, and $C_{1-6}$ haloalkoxy.

According to still another exemplary embodiment, $R_1$ and $R_2$ may be taken together with nitrogen to which they are attached to form dihydropyrrolinyl or tetrahydropyridinyl which is unsubstituted or substituted with $C_{1-4}$ alkyl, or $R_1$ and $R_2$ may be taken together with nitrogen to which they are attached to form piperidinyl or pyrrolidinyl which is substituted with $C_{1-4}$ alkyl in at least one position thereof, and $R_3$ may be hydrogen; $C_{1-6}$ alkyl; phenyl; or $C_{1-4}$ alkyl substituted with phenyl, wherein the phenyl is unsubstituted or substituted with at least one non-hydrogen substituent selected from the group consisting of halogen, $C_{1-4}$ alkoxy, $C_{1-4}$ haloalkyl, and $C_{1-4}$ haloalkoxy.

According to still another exemplary embodiment, $R_1$ and $R_2$ may be taken together with nitrogen to which they are attached to form dihydropyrrolinyl or tetrahydropyridinyl which is unsubstituted or substituted with $C_{1-2}$ alkyl, or $R_1$ and $R_2$ may be taken together with nitrogen to which they are attached to form piperidinyl or pyrrolidinyl substituted with one or two $C_{1-2}$ alkyl groups, and $R_3$ may be hydrogen; $C_{3-6}$ alkyl; phenyl; or $C_{1-2}$ alkyl substituted with phenyl, wherein the phenyl is unsubstituted or substituted with at least one non-hydrogen substituent selected from the group consisting of halogen, $C_{1-2}$ alkoxy, $C_{1-2}$ haloalkyl, and $C_{1-2}$ haloalkoxy.

According to yet another exemplary embodiment, $R_1$ and $R_2$ may be taken together with nitrogen to which they are attached to form dihydropyrrolinyl or tetrahydropyridinyl which is unsubstituted or substituted with methyl, or $R_1$ and $R_2$ may be taken together with nitrogen to which they are attached to form piperidine, and $R_3$ may be hydrogen; butyl; propyl; hexyl; phenyl; or methyl substituted with phenyl, wherein the piperidine is substituted with one or two methyl groups in at least one of positions 2, 3, 5 and 6, and the phenyl is unsubstituted or substituted with at least one non-hydrogen substituent selected from the group consisting of halogen, methoxy, trihalomethyl, and trihalomethoxy.

According to one exemplary embodiment, the compound of Formula 1 may include

N1-1,2-dihydropyrrole-N5-(4-trifluoromethoxy)phenyl biguanide;
N1-1,2-dihydropyrrole-N5-(4-trifluoromethyl)phenyl biguanide;
N1-1,2-dihydropyrrole-N5-(3-trifluoromethyl)phenyl biguanide;
N1-1,2-dihydropyrrole-N5-(4-fluoro)phenyl biguanide;
N1-1,2-dihydropyrrole-N5-(4-chloro)phenyl biguanide;
N1-1,2-dihydropyrrole-N5-(4-bromo)phenyl biguanide;
N1-1,2-dihydropyrrole-N5-(3-chloro, 4-trifluoromethoxy)phenyl biguanide;
N1-1,2,3,6-tetrahydropyridine-N5-(3-chloro, 4-trifluoromethoxy)phenyl biguanide;
N1-1,2-dihydropyrrole-N5-(3-trifluoromethyl)benzyl biguanide;
N1-1,2-dihydropyrrole-N5-(4-trifluoromethyl)benzyl biguanide;
N1-1,2-dihydropyrrole-N5-(3-trifluoromethoxy)benzyl biguanide;
N1-(3-methyl)-1,2-dihydropyrrole-N5-(4-trifluoromethoxy)phenyl biguanide;
N1-(3-methyl)-1,2-dihydropyrrole-N5-(4-trifluoromethyl)phenyl biguanide;
N1-(3-methyl)-1,2-dihydropyrrole-N5-(4-chloro)phenyl biguanide;
N1-(3-methyl)-1,2-dihydropyrrole-N5-(4-chloro, 3-trifluoromethyl)phenyl biguanide;
N1-(3-methyl)-1,2-dihydropyrrole-N5-(3-trifluoromethyl)phenyl biguanide;
N1-(3-methyl)-1,2-dihydropyrrole-N5-(4-fluoro)phenyl biguanide;
N1-(3-methyl)-1,2-dihydropyrrole-N5-(4-bromo)phenyl biguanide;
N1-(3-methyl)-1,2-dihydropyrrole-N5-(4-methoxyl)phenyl biguanide;
N1-(3-methyl)-1,2-dihydropyrrole-N5-(3,4-dimethoxy)phenyl biguanide;
N1-(3-methyl)-1,2-dihydropyrrole-N5-(4-trifluoromethoxy)benzyl biguanide;
N1-(3-methyl)-1,2-dihydropyrrole-N5-(3-trifluoromethoxy)phenyl biguanide;
N1-(3-methyl)-1,2-dihydropyrrole-N5-(4-trifluoromethyl)benzyl biguanide;
N1-(3-methyl)-1,2-dihydropyrrole-N5-(4-chloro, 3-trifluoromethyl)benzyl biguanide;
N1-1,2,3,6-tetrahydropyridine-N5-(4-trifluoromethoxy)phenyl biguanide;
N1-1,2,3,6-tetrahydropyridine-N5-(4-trifluoromethyl)phenyl biguanide;
N1-1,2,3,6-tetrahydropyridine-N5-(3-trifluoromethoxy)phenyl biguanide;
N1-1,2,3,6-tetrahydropyridine-N5-(3-trifluoromethyl)phenyl biguanide;
N1-1,2,3,6-tetrahydropyridine-N5-(4-fluoro, 3-trifluoromethyl)phenyl biguanide;
N1-1,2,3,6-tetrahydropyridine-N5-(4-chloro, 3-trifluoromethoxy)phenyl biguanide;
N1-1,2,3,6-tetrahydropyridine-N5-(3-fluoro,4-trifluoromethoxy)phenyl biguanide;
N1-1,2,3,6-tetrahydropyridine-N5-(4-chloro)phenyl biguanide;
N1-1,2,3,6-tetrahydropyridine-N5-(4-bromo)phenyl biguanide;
N1-1,2,3,6-tetrahydropyridine-N5-(4-fluoro)phenyl biguanide;
N1-1,2,3,6-tetrahydropyridine-N5-(3,5-dimethoxy)phenyl biguanide;
N1-1,2,3,6-tetrahydropyridine-N5-phenyl biguanide;
N1-1,2,3,6-tetrahydropyridine-N5-(4-methoxyl)phenyl biguanide;
N1-1,2,3,6-tetrahydropyridine-N5-(3-methoxyl)phenyl biguanide;
N1-1,2-dihydropyrrole-N5-(4-methoxyl)phenyl biguanide;
N1-1,2-dihydropyrrole-N5-(3-methoxyl)phenyl biguanide;
N1-1,2-dihydropyrrole-N5-phenyl biguanide;
N1-1,2-dihydropyrrole-N5-(3,5-dimethoxy)phenyl biguanide;
N1-1,2-dihydropyrrole-N5-(4-fluoro, 3-trifluoromethyl)phenyl biguanide;

N1-1,2-dihydropyrrole-N5-(3-fluoro, 4-trifluoromethyl)phenyl biguanide;
N1-1,2,3,6-tetrahydropyridine-N5-(4-methyl)phenyl biguanide;
N1-1,2,3,6-tetrahydropyridine-N5-(3-methyl)phenyl biguanide;
N1-1,2-dihydropyrrole-N5-(4-methyl)phenyl biguanide;
N1-1,2-dihydropyrrole-N5-(3-methyl)phenyl biguanide;
N1-1,2-dihydropyrrole-N5-(3-trifluoromethoxy)phenyl biguanide;
N1-1,2,3,6-tetrahydropyridine-N5-hexyl biguanide;
N1-1,2,3,6-tetrahydropyridine-N5-(4-trifluoromethoxy)benzyl biguanide;
N1-1,2,3,6-tetrahydropyridine-N5-(3-trifluoromethoxy)benzyl biguanide;
N1-1,2,3,6-tetrahydropyridine-N5-(4-trifluoromethyl)benzyl biguanide;
N1-1,2,3,6-tetrahydropyridine-N5-(3-trifluoromethyl)benzyl biguanide;
N1-1,2,3,6-tetrahydropyridine-N5-(4-chloro, 3-trifluoromethyl)benzyl biguanide;
N1-1,2,3,6-tetrahydropyridine-N5-butyl biguanide;
N1-1,2,3,6-tetrahydropyridine-N5-propyl biguanide; N1-1,2,3,6-tetrahydropyridine biguanide; N1-(3-methyl)piperidine-N5-(3-trifluoromethyl)benzyl biguanide;
N1-(3-methyl)piperidine-N5-(4-chloro)benzyl biguanide;
N1-(3-methyl)piperidine-N5-(4-fluoro)phenyl biguanide;
N1-(3-methyl)piperidine-N5-(4-bromo)phenyl biguanide;
N1-(3-methyl)piperidine-N5-(4-chloro, 3-trifluoromethyl)phenyl biguanide;
N1-(3-methyl)piperidine-N5-(3-fluoro, 4-trifluoromethyl)phenyl biguanide;
N1-(3-methyl)piperidine-N5-(4-fluoro, 3-trifluoromethyl)phenyl biguanide;
N1-(2-methyl)piperidine-N5-(4-trifluoromethoxy)phenyl biguanide;
N1-(2-methyl)piperidine-N5-(3-trifluoromethoxy)phenyl biguanide;
N1-(2-methyl)piperidine-N5-(4-trifluoromethyl)phenyl biguanide;
N1-(3-methyl)piperidine-N5-(3-fluoro, 4-trifluoromethoxy)phenyl biguanide;
N1-(3-methyl)piperidine-N5-(3-fluoro, 4-trifluoromethoxy)phenyl biguanide;
N1-(2-methyl)piperidine-N5-(4-chloro)phenyl biguanide;
N1-(2-methyl)piperidine-N5-(4-fluoro, 3-trifluoromethyl)phenyl biguanide;
N1-(2-methyl)piperidine-N5-(3-trifluoromethyl)phenyl biguanide;
N1-(2-methyl)piperidine-N5-(4-chloro, 3-trifluoromethyl)phenyl biguanide;
N1-(3-methyl)piperidine-N5-(4-trifluoromethyl)phenyl biguanide;
N1-(3-methyl)piperidine-N5-(4-trifluoromethoxy)phenyl biguanide;
N1-(3-methyl)piperidine-N5-(3-trifluoromethoxy)phenyl biguanide;
N1-(3-methyl)piperidine-N5-(4-trifluoromethoxy)benzyl biguanide;
N1-(3-methyl)piperidine-N5-(4-fluoro, 3-trifluoromethyl)phenyl biguanide;
N1-(3-methyl)piperidine-N5-(4-trifluoromethyl)benzyl biguanide;
N1-(3-methyl)piperidine-N5-(4-chloro)phenyl biguanide;
N1-(3-methyl)piperidine-N5-(3-trifluoromethyl)phenyl biguanide;
N1-(2,6-dimethyl)piperidine-N5-(4-trifluoromethoxy)phenyl biguanide;
N1-(2,6-dimethyl)piperidine-N5-(3-trifluoromethoxy)phenyl biguanide;
N1-(2,6-dimethyl)piperidine-N5-(4-trifluoromethyl)phenyl biguanide;
N1-(2,6-dimethyl)piperidine-N5-(3-trifluoromethyl)phenyl biguanide;
N1-(2,6-dimethyl)piperidine-N5-(4-fluoro, 3-trifluoromethyl)phenyl biguanide;
N1-(2,6-dimethyl)piperidine-N5-(4-chloro, 3-trifluoromethyl)phenyl biguanide;
N1-(2,6-dimethyl)piperidine-N5-(3-fluoro, 4-trifluoromethoxy)phenyl biguanide;
N1-(2,6-dimethyl)piperidine-N5-(4-chloro)phenyl biguanide;
N1-(2,6-dimethyl)piperidine-N5-(4-bromo)phenyl biguanide; or
N1-(2,6-dimethyl)piperidine-N5-(4-fluoro)phenyl biguanide.

Meanwhile, a pharmaceutically acceptable salt of the compound of Formula 1 according to the present invention may be an acid addition salt formed using an organic acid or an inorganic acid. For example, the organic acid may include formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, dichloroacetic acid, aminooxy acetic acid, benzensulfonic acid, 4-toluenesulfonic acid and methanesulfonic acid; and the inorganic acid may include, for example, hydrochloric acid, hydrobromic acid, sulfuric acid, phosphoric acid, nitric acid, carbonic acid and boric acid. For example, the above-described acid addition salt may be prepared by a typical method of preparing a salt, including a) directly mixing the compound of Formula 1 and an acid, b) dissolving one of the compound and an acid in a solvent or a hydrated solvent and mixing the resulting solution, or c) mixing the compound of Formula 1 and the acid in the presence of a solvent or a hydrated solvent.

According to one exemplary embodiment, the pharmaceutically acceptable salt of the compound represented by Formula 1 may be a salt of an acid selected from the group consisting of formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, benzensulfonic acid, p-toluenesulfonic acid, methanesulfonic acid, dichloroacetic acid, aminooxy acetic acid, hydrochloric acid, hydrobromic acid, sulfuric acid, phosphoric acid, nitric acid, carbonic acid, and boric acid.

The compound of Formula 1 according to the present invention may be prepared by several methods.

According to one exemplary embodiment, there is provided a method of preparing a compound represented by the following Formula 1, which includes reacting a compound of the following Formula 2 with a dicyanamide in an organic solvent to obtain a compound of the following Formula 3; and reacting the compound of the following Formula 3 with a compound of the following Formula 4 in an organic solvent to obtain the compound of the following Formula 1:

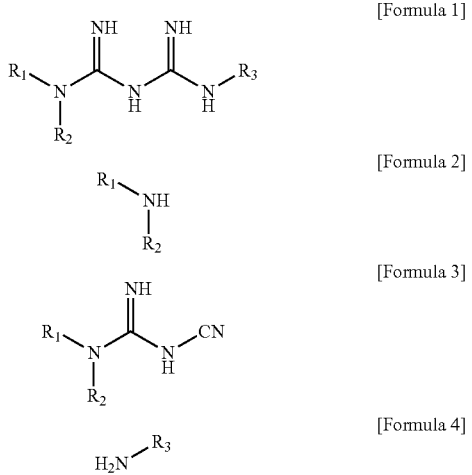

[Formula 1]

[Formula 2]

[Formula 3]

[Formula 4]

In Formulas 1 to 4, $R_1$, $R_2$ and $R_3$ are the same as defined in Formula 1.

For example, the preparation method may be illustrated in the following Scheme 1, and will be described by operations, as follows.

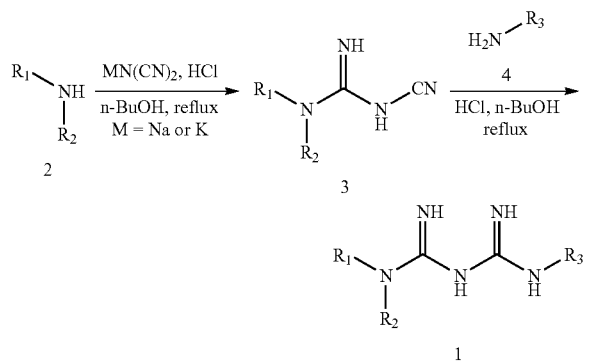

[Scheme 1]

In the method of preparing the compound of Formula 1, the cyanoguanidine compound of Formula 3 used as an intermediate may be obtained by reacting the cyclic amine of Formula 2 with a dicyanamide such as sodium or potassium dicyanamide in an organic solvent in the presence of an acid. Then, the compound of Formula 1 may be obtained by refluxing the obtained cyanoguanidine compound of Formula 3 with the compound of Formula 4 in an organic solvent.

An amount of the dicyanamide used for preparation of the cyanoguanidine compound of Formula 3 is equivalent to approximately 1 to 3 moles with respect to the compound of Formula 2, and an amount of the acid used is equivalent to approximately 1 to 2 moles with respect to the compound of Formula 2. Upon preparation of the compound of Formula 2, methanol, ethanol, propanol, butanol, pentanol, acetonitrile, benzene, toluene, 1,4-dioxane, N,N-dimethylamide, and the like may be, for example, used as the organic solvent, and hydrochloric acid, sulfuric acid, nitric acid, hydrobromic acid, 4-toluenesulfonic acid, and the like may be, used as the acid. The reaction temperature of the compound of Formula 2 and the dicyanamide may be in a range of 60 to 140° C., and the reaction time may be in a range of 3 to 24 hours.

After the cyanoguanidine compound of Formula 3 obtained above is dissolved in an organic solvent, the compound of Formula 4 and an acid are added, and then stirred under reflux. In this case, an amount of the compound of Formula 4 is equivalent to approximately 1 to 2 moles with respect to the compound of Formula 3, and an amount of the acid is equivalent to approximately 1 to 2 moles with respect to the compound of Formula 3. For example, the organic solvent used in reaction of the compound of Formula 3 and the compound of Formula 4 may include methanol, ethanol, propanol, butanol, pentanol, acetonitrile, benzene, toluene, 1,4-dioxane, N,N-dimethylamide, and the like, and the acid may, for example, include hydrochloric acid, sulfuric acid, nitric acid, hydrobromic acid, 4-toluenesulfonic acid, and the like. In this case, the reaction temperature may be in a range of a reflux temperature of the solvent used (i.e., 120 to 140° C. for butanol), and the reaction time may be in a range of 6 to 24 hours. When the reaction is completed, the resulting reaction solution is filtered. Thereafter, a pH of the filtered reaction solution may be controlled to approximately 4 to 5 using an acid such as, hydrochloric acid. Then, the resulting reaction solution may be concentrated and purified to yield the compound of Formula 1 or a pharmaceutically acceptable salt thereof according to the present invention.

The compound of Formula 1 or the pharmaceutically acceptable salt thereof produced in this way may be useful in performing anticancer treatment including inhibition of cancer metastasis and cancer recurrence by AMPK activation, even when administered in a small dose compared with conventional drugs, as will be confirmed in the following Examples.

Therefore, the present invention provides a medicine including the compound of Formula 1 or the pharmaceutically acceptable salt thereof as an active ingredient.

Another aspect of the present invention provides a pharmaceutical composition for preventing or treating a cancer, which includes the compound of Formula 1 or the pharmaceutically acceptable salt thereof as an active ingredient, the use of the compound of Formula 1 or the pharmaceutically acceptable salt thereof to prepare a medicine for preventing or treating the disease, and a method of preventing or treating the disease including administering a therapeutically effective amount of the compound of Formula 1 or the pharmaceutically acceptable salt thereof to a subject.

The pharmaceutical composition of the present invention includes at least one pharmaceutically acceptable carrier in addition to the active ingredient. As used in this specification, the term pharmaceutically acceptable carrier refers to a known pharmaceutically acceptable excipient, which is useful to formulate a pharmaceutically active compound for administration, and is substantially non-toxic and non-sensitive under the conditions used. An exact ratio of the excipient is determined by standard pharmaceutical practice, as well as solubility, chemical characteristics and selected route for administration of the active compound.

The pharmaceutical composition of the present invention may be formulated in a form suitable for a desired administration method using a suitable and physiologically available adjuvant such as an excipient, a disintegrating agent, a sweetening agent, a binder, a coating agent, a swelling agent, a lubricating agent, a glossing agent, a flavoring agent, or the like.

The pharmaceutical composition may be formulated as a tablet, a capsule, a pill, a granule, a powder, an injection or a liquid, but the present invention is not limited thereto.

The formulation and the pharmaceutically acceptable carrier of the pharmaceutical composition may be properly selected according to the techniques known in the related art, and, for example, may be selected with reference to the following documents: (Urquhart et al., Lancet, 16:367, 1980); (Lieberman et al., PHARMACEUTICAL DOSAGE FORMS-DISPERSE SYSTEMS, 2nd ed., vol. 3, 1998); (Ansel et al., PHARMACEUTICAL DOSAGE FORMS & DRUG DELIVERY SYSTEMS, 7th ed., 2000); (Martindale, THE EXTRA PHARMACOPEIA, 31st ed.); (Remington's PHARMACEUTICAL SCIENCES, 16th-20th editions); (THE PHARMACOLOGICAL BASIS OF THERAPEUTICS, Goodman and Gilman, eds., 9th ed., 1996); and (Wilson and Gisvolds' TEXTBOOK OF ORGANIC MEDICINAL AND PHARMACEUTICAL CHEMISTRY, Delgado and Remers, eds., 10th ed., 1998). Also, principals of formulating a pharmaceutical composition may be described, for example, with reference to the following documents: (Platt, Clin Lab Med, 7:289-99, 1987); (Aulton, PHARMACEUTICS: THE SCIENCE OF DOSAGE FORM DESIGN, Churchill Livingstone, N.Y., 1988); (EXTEMPORANEOUS ORAL LIQUID DOSAGE PREPARATIONS, CSHP, 1998); and (Drug Dosage, J Kans Med Soc, 70(1): 30-32, 1969).

According to one exemplary embodiment, the pharmaceutical composition may be used together with a second drug.

According to the present invention, the term second drug refers to another pharmaceutically active ingredient in addition to the biguanide derivative according to the present invention. The compound of Formula 1 or the pharmaceutically acceptable salt thereof according to the present invention may be used to treat a variety of diseases, as described above. As a result, the compound of Formula 1 or the pharmaceutically acceptable salt thereof according to the present invention may be used together with a second drug for effectively treating respective diseases. For example, the second drug may be an anticancer agent, an anti-hyperglycemic agent, an anti-obesity agent, etc., which includes an active ingredient different from the compound of Formula 1 or the pharmaceutically acceptable salt thereof.

When the compound of Formula 1 or the pharmaceutically acceptable salt thereof according to the present invention and the second drug are able to be administered in the same manner, the compound of Formula 1 or the pharmaceutically acceptable salt thereof may be formulated together with the second drug to be provided in the form of a composite preparation.

Meanwhile, according to the present invention, the term subject refers to a warm-blooded animal such as a mammal with a specific condition, disorder or disease. For example, the subject may be a human, an orangutan, a chimpanzee, a mouse, a rat, a dog, a cow, a chicken, a pig, a goat, a sheep, etc., but the present invention is not limited thereto.

Also, the term treating includes relieving a symptom, temporarily or permanently eliminating causes of the symptom, and preventing or hindering occurrence of the symptom or progression of the above-described condition, disorder or disease, but the present invention is not limited thereto.

An effective amount of the active ingredient of the pharmaceutical composition according to the present invention refers to an amount required to treat a disease. Therefore, the effective amount of the active ingredient may be adjusted according to various factors such as kinds and severity of a disease, kinds and contents of an active ingredient and other ingredients included in the composition, kinds of a formulation, age, body weight, general medical conditions, sex and diet of a patient, duration and route of administration, a release rate of the composition, treatment duration, and the number of drugs used together. In the case of adults, for example, the compound of Formula 1 may be administered in a total dose of 50 to 3,000 mg/kg when administered once to several times a day.

Advantageous Effects of Invention

The N1-cyclic amine-N5-substituted biguanide derivative of Formula 1 according to the present invention can be highly useful in treating a cancer since the N1-cyclic amine-N5-substituted biguanide derivative of Formula 1 has an effect of inhibiting cancer cell proliferation, cancer metastasis and recurrence even when administered in a small dose compared with conventional drugs.

Mode for the Invention

The advantages and features of the present invention and the method of revealing them will be explicit from the following examples described in detail. However, it is to be distinctly understood that the present invention is not limited thereto but may be otherwise variously embodied and practiced. It is obvious that the following examples are to complete the disclosure of the invention and to indicate the scope of the present invention to a skilled artisan completely, and the present invention will be defined only by the scope of the claims.

EXAMPLES

Example 1

Synthesis of N1-2,5-dihydropyrrole cyanoguanidine

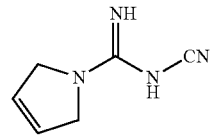

2,5-Dihydropyrrole hydrochloride (0.75 g, 7.104 mmol) and sodium dicyanamide (0.63 g, 7.104 mmol) were dissolved in a butanol (20 mL) solution, and then stirred for 3 hours under reflux. After completion of the reaction was confirmed, sodium chloride formed by filtering the reaction mixture was removed, and the filtrate was then concentrated at a reduced pressure. The concentrate was dissolved in methanol (2 mL), and ethyl acetate (5 mL) was then added thereto, and stirred at room temperature for an hour. The formed solid was filtered and the filtrate was washed with ethyl acetate (2×20 mL). The filtrate was dried at a reduced pressure to obtain a white solid target compound (0.90 g, 93%).

$^1$H NMR (600 MHz, CD$_3$OD) δ 5.89 (m, 2H), 4.16 (m, 4H); LC-MS m/z 137.2 [M+1]$^+$

Example 2

Synthesis of N1-1,2,3,6-tetrahydropyridine cyanoguanidine

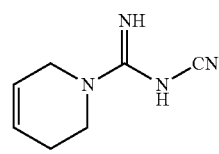 [SMILES: N#CNC(=N)N1CC=CCC1]

A white solid target compound (2.23 g, 59.2%) was prepared in the same manner as in Example 1, except that 1,2,3,6-tetrahydropyridine was used instead of the 2,5-dihydropyrrole hydrochloride used in Example 1.

$^1$H NMR (600 MHz, CD$_3$OD) δ 5.90 (d, 1H), 5.69 (d, 1H), 3.93 (t, 2H), 3.59 (t, 2H), 2.18 (m, 2H); LC-MS m/z 151.2 [M+1]$^+$

Example 3

Synthesis of N1-3-methyl-2,5-dihydropyrrole cyanoguanidine

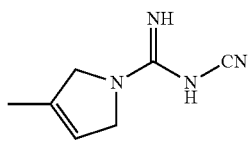

A white solid target compound (3.12 g, 83%) was prepared in the same manner as in Example 1, except that 3-methyl-2,5-dihydropyrrole was used instead of the 2,5-dihydropyrrole hydrochloride used in Example 1.

$^1$H NMR (600 MHz, CD$_3$OD) δ 5.45 (br s, 1H), 4.80 (m, 2H), 4.10 (m, 2H) 7.16 (s, 3H); LC-MS m/z 151.2 [M+1]$^+$

Example 4

Preparation of N1-1,2-dihydropyrrole-N5-(4-trifluoromethoxy)phenyl biguanide hydrochloride

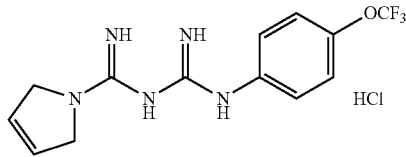 [SMILES: N=C(NC(=N)N1CC=CC1)Nc1ccc(OC(F)(F)F)cc1 ; Cl]

(4-Trifluoromethoxy)phenylamine (390 mg, 2.20 mmol) was dissolved in a butanol (10 mL) solution at room temperature, and concentrated hydrochloric acid (0.18 mL, 2.20 mmol) was added to the resulting solution, and then stirred for 30 minutes. The N1-2,5-dihydropyrrole cyanoguanidine (300 mg, 2.20 mmol) obtained in Example 1 was added to the reaction mixture, and then stirred for an hour under reflux. The reaction mixture was stirred at room temperature for an hour, and the formed solid was filtered. Then, the filtrate was dried at a reduced pressure to obtain a white solid target compound (265 mg, 34%).

$^1$H NMR (600 MHz, CD$_3$OD) δ 3.94 (m, 2H), 3.71 (m, 2H), 3.47 (m, 1H), 3.34 (s, 3H), 2.90 (m, 1H), 2.57 (m, 1H), 1.71 (m, 10H), 1.18 (m, 1H), 0.89 (s, 3H); LC-MS m/z 282.2 [M+1]$^+$; mp 172-174° C.

Target compounds of the following Examples 5 to 61 were prepared in the same manner as in Example 4, except that the cyanoguanidine and amine compounds synthesized in Examples 2 and 3, which corresponded to the target compounds, were used respectively instead of the N1-2,5-dihydropyrrole cyanoguanidine synthesized in Example 1 and the (4-trifluoromethoxy)phenylamine used in Example 4.

Example 5

Preparation of N1-1,2-dihydropyrrole-N5-(4-trifluoromethyl)phenyl biguanide hydrochloride

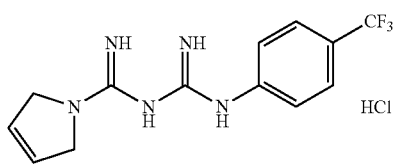 [SMILES: N=C(NC(=N)N1CC=CC1)Nc1ccc(C(F)(F)F)cc1 ; Cl]

$^1$H NMR (600 MHz, CD$_3$OD) δ 7.58 (m, 4H), 5.91 (m, 2H), 4.27 (m, 4H); LC-MS m/z 298.2 [M+1]$^+$; mp 254-256° C.

Example 6

Preparation of N1-1,2-dihydropyrrole-N5-(3-trifluoromethyl)phenyl biguanide hydrochloride

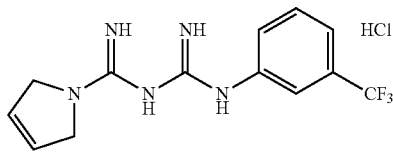 [SMILES: N=C(NC(=N)N1CC=CC1)Nc1cccc(C(F)(F)F)c1 ; Cl]

$^1$H NMR (600 MHz, CD$_3$OD) δ 7.79 (m, 1H), 7.56 (m, 1H), 7.46 (m, 1H), 7.34 (m, 1H), 5.91 (s, 2H), 4.20 (m, 4H); LC-MS m/z 298.2 [M+1]$^+$; mp 276-278° C.

Example 7

Preparation of N1-1,2-dihydropyrrole-N5-(4-fluoro)phenyl biguanide hydrochloride

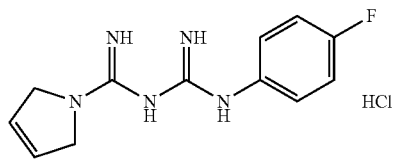 [SMILES: N=C(NC(=N)N1CC=CC1)Nc1ccc(Cl)cc1 ; Cl]

$^1$H NMR (600 MHz, CD$_3$OD) δ 7.33 (m, 2H), 7.04 (m, 2H), 5.90 (m, 2H), 4.17 (m, 4H); LC-MS m/z 248.2 [M+1]$^+$; mp 263-265° C.

Example 8

N1-1,2-dihydropyrrole-N5-(4-chloro)phenyl biguanide hydrochloride

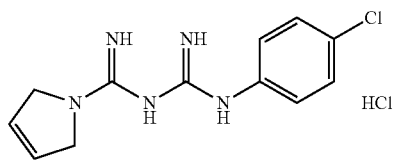 [SMILES: N=C(NC(=N)N1CC=CC1)Nc1ccc(Br)cc1 ; Cl]

$^1$H NMR (600 MHz, CD$_3$OD) δ 7.29 (m, 4H), 5.90 (m, 2H), 4.20 (m, 4H); LC-MS m/z 264.2 [M+1]$^+$; mp 264-266° C.

Example 9

N1-1,2-dihydropyrrole-N5-(4-bromo)phenyl biguanide hydrochloride

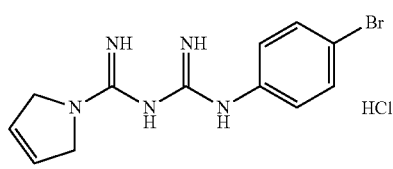

$^1$H NMR (600 MHz, CD$_3$OD) δ 7.42 (m, 2H), 7.30 (m, 2H), 5.90 (m, 2H), 4.24 (m, 4H); LC-MS m/z 309.0 [M+1]$^+$; mp 263-265° C.

Example 10

N1-1,2-dihydropyrrole-N5-(3-chloro,4-trifluoromethoxy)phenyl biguanide hydrochloride

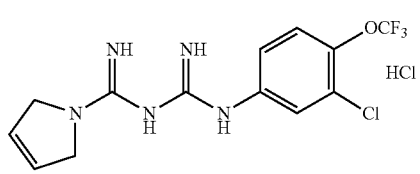 [SMILES: N=C(NC(=N)N1CC=CC1)Nc1ccc(OC(F)(F)F)c(Cl)c1 ; Cl]

$^1$H NMR (600 MHz, CD$_3$OD) δ 7.79 (m, 1H), 7.42 (m, 2H), 5.99 (m, 2H), 4.30 (m, 4H); LC-MS m/z 348.2 [M+1]$^+$; mp 270-272° C.

Example 11

N1-1,2,3,6-tetrahydropyridine-N5-(3-chloro,4-trifluoromethoxy) phenyl biguanide hydrochloride

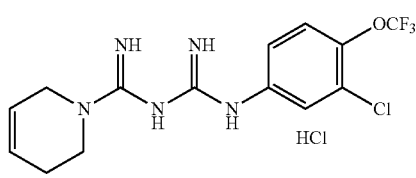 [SMILES: N=C(NC(=N)N1CC=CCC1)Nc1ccc(OC(F)(F)F)c(Cl)c1 ; Cl]

$^1$H NMR (600 MHz, CD$_3$OD) δ 7.70 (m, 1H), 7.33 (m, 2H), 5.94 (m, 1H), 5.73 (m, 1H), 3.99 (m, 2H), 3.63 (m, 2H), 2.23 (m, 2H); LC-MS m/z 362.2 [M+1]$^+$; mp 250-252° C.

Example 12

N1-1,2-dihydropyrrole-N5-(3-trifluoromethyl)benzyl biguanide hydrochloride

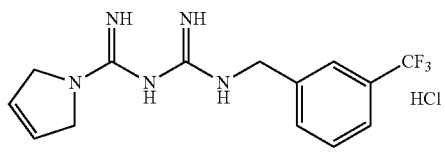 [SMILES: N=C(NCc1cccc(C(F)(F)F)c1)NC(=N)N1CC=CC1 ; Cl]

$^1$H NMR (600 MHz, CD$_3$OD) δ 7.70 (m, 4H), 5.89 (m, 2H), 4.52 (m, 2H), 4.23 (m, 4H); LC-MS m/z 312.2 [M+1]$^+$; mp 156-158° C.

Example 13

N1-1,2-dihydropyrrole-N5-(4-trifluoromethyl)benzyl biguanide hydrochloride

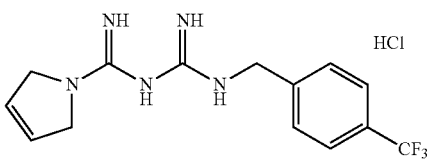 [SMILES: N=C(NCc1ccc(C(F)(F)F)cc1)NC(=N)N1CC=CC1 ; Cl]

$^1$H NMR (600 MHz, CD$_3$OD) δ 7.45 (m, 2H), 7.62 (m, 2H), 5.86 (m, 2H), 4.19 (m, 2H), 4.13 (m, 4H); LC-MS m/z 312.2 [M+1]$^+$; mp 268-270° C.

Example 14

N1-1,2-dihydropyrrole-N5-(3-trifluoromethoxy) benzyl biguanide hydrochloride

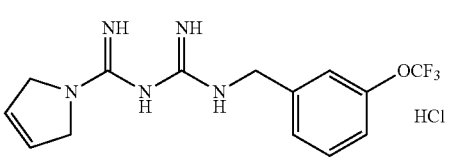 [SMILES: N=C(NCc1cccc(OC(F)(F)F)c1)NC(=N)N1CC=CC1 ; Cl]

$^1$H NMR (600 MHz, CD$_3$OD) δ 7.33 (m, 4H), 5.88 (m, 2H), 4.47 (s, 2H), 4.18 (m, 4H); LC-MS m/z 328.2 [M+1]$^+$; mp 218-220° C.

Example 15

N1-(3-methyl)-1,2-dihydropyrrole-N5-(4-trifluoromethoxy)phenyl biguanide hydrochloride

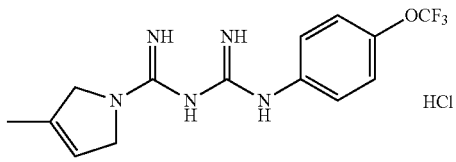 [SMILES: CC1=CCN(C(=N)NC(=N)Nc2ccc(OC(F)(F)F)cc2)C1 ; Cl]

$^1$H NMR (600 MHz, CD$_3$OD) δ 7.41 (m, 2H), 7.16 (m, 2H), 5.46 (m, 1H), 4.10 (m, 3H), 1.77 (m, 3H); LC-MS m/z 328.2 [M+1]$^+$; mp 279-281° C.

Example 16

N1-(3-methyl)-1,2-dihydropyrrole-N5-(4-trifluoromethyl)phenyl biguanide hydrochloride

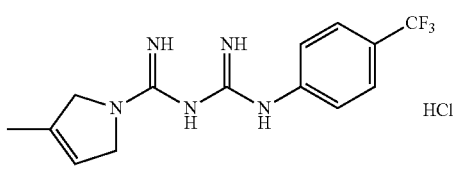 [SMILES: CC1=CCN(C(=N)NC(=N)Nc2ccc(C(F)(F)F)cc2)C1 ; Cl]

$^1$H NMR (600 MHz, CD$_3$OD) δ 7.62 (m, 4H), 5.56 (m, 1H), 4.21 (m, 4H), 1.87 (m, 3H); LC-MS m/z 312.2 [M+1]$^+$; mp 272-274° C.

Example 17

N1-(3-methyl)-1,2-dihydropyrrole-N5-(4-chloro)phenyl biguanide hydrochloride

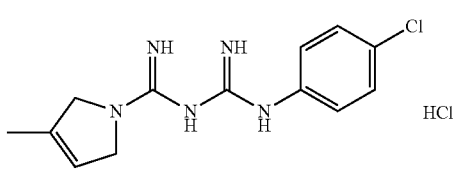 [SMILES: CC1=CCN(C(=N)NC(=N)Nc2ccc(Cl)cc2)C1 ; Cl]

$^1$H NMR (600 MHz, CD$_3$OD) δ 7.36 (m, 2H), 7.29 (m, 2H), 5.50 (m, 1H), 4.13 (m, 4H), 1.80 (m, 3H); LC-MS m/z 278.2 [M+1]$^+$; mp 264-268° C.

Example 18

N1-(3-methyl)-1,2-dihydropyrrole-N5-(4-chloro, 3-trifluoromethyl)phenyl biguanide hydrochloride

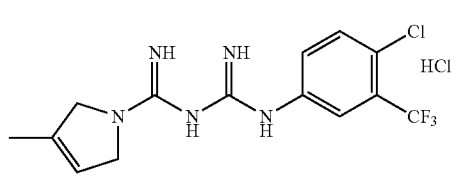 [SMILES: CC1=CCN(C(=N)NC(=N)Nc2ccc(Cl)c(C(F)(F)F)c2)C1 ; Cl]

$^1$H NMR (600 MHz, CD$_3$OD) δ 7.92 (m, 1H), 7.58 (m, 1H), 7.50 (m, 1H), 5.51 (s, 1H), 4.17 (m, 4H), 1.82 (m, 3H); LC-MS m/z 346.2 [M+1]$^+$; mp 274-276° C.

Example 19

N1-(3-methyl)-1,2-dihydropyrrole-N5-(3-trifluoromethyl)phenyl biguanide hydrochloride

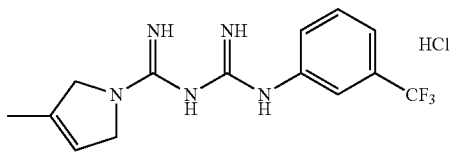 [SMILES: CC1=CCN(C(=N)NC(=N)Nc2cccc(C(F)(F)F)c2)C1 ; Cl]

$^1$H NMR (600 MHz, CD$_3$OD) δ 7.80 (m, 1H), 7.57 (m, 1H), 7.42 (m, 1H), 7.34 (m, 1H), 5.51 (m, 1H), 4.15 (m, 4H), 1.81 (m, 3H); LC-MS m/z 312.2 [M+1]$^+$; mp 282-284° C.

Example 20

N1-(3-methyl)-1,2-dihydropyrrole-N5-(4-fluoro)phenyl biguanide hydrochloride

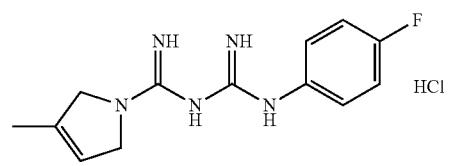 [SMILES: CC1=CCN(C(=N)NC(=N)Nc2ccc(F)cc2)C1 ; Cl]

$^1$H NMR (600 MHz, CD$_3$OD) δ 7.34 (m, 2H), 7.04 (m, 2H), 5.50 (m, 1H), 4.12 (m, 4H), 1.80 (m, 3H); LC-MS m/z 262.1 [M+1]$^+$; mp 270-272° C.

Example 21

N1-(3-methyl)-1,2-dihydropyrrole-N5-(4-bromo)phenyl biguanide hydrochloride

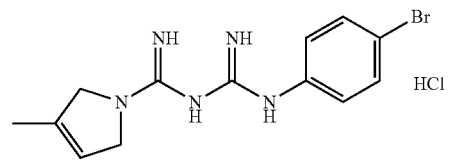 [SMILES: CC1=CCN(C(=N)NC(=N)Nc2ccc(Br)cc2)C1 ; Cl]

$^1$H NMR (600 MHz, CD$_3$OD) δ 7.45 (m, 2H), 7.33 (m, 2H), 5.52 (m, 1H), 4.16 (m, 4H), 1.83 (m, 3H); LC-MS m/z 323.0 [M+1]$^+$; mp 272-274° C.

Example 22

N1-(3-methyl)-1,2-dihydropyrrole-N5-(4-methoxyl)phenyl biguanide hydrochloride

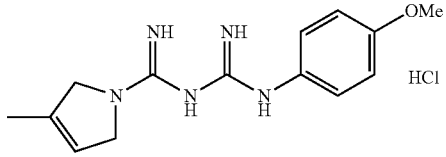 [SMILES: COc1ccc(NC(=N)NC(=N)N2CC=C(C)C2)cc1 ; Cl]

$^1$H NMR (600 MHz, CD$_3$OD) δ 7.24 (m, 2H), 6.87 (m, 2H), 5.48 (s, 1H), 3.32 (s, 3H), 1.78 (m, 3H); LC-MS m/z 274.2 [M+1]$^+$; mp 263-265° C.

Example 23

N1-(3-methyl)-1,2-dihydropyrrole-N5-(3,4-dimethoxy)phenyl biguanide hydrochloride

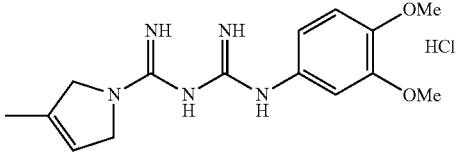 [SMILES: COc1ccc(NC(=N)NC(=N)N2CC=C(C)C2)cc1OC ; Cl]

$^1$H NMR (600 MHz, CD$_3$OD) δ 6.58 (m, 2H), 6.26 (m, 1H), 5.52 (m, 1H), 4.18 (m, 4H), 3.30 (s, 3H), 1.83 (m, 3H); LC-MS m/z 304.2 [M+1]$^+$; mp 261-263° C.

Example 24

N1-(3-methyl)-1,2-dihydropyrrole-N5-(4-trifluoromethoxy)benzyl biguanide hydrochloride

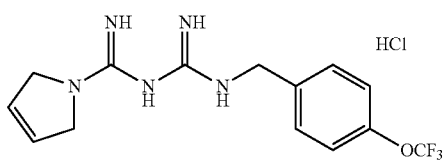 [SMILES: N=C(NCc1ccc(OC(F)(F)F)cc1)NC(=N)N1CC=CC1 ; Cl]

$^1$H NMR (600 MHz, CD$_3$OD) δ 7.59 (m, 1H), 7.43 (m, 2H), 7.35 (m, 1H), 7.25 (m, 1H), 5.46 (m, 1H), 4.43 (m, 2H), 4.15 (m, 2H), 1.81 (m, 3H); LC-MS m/z 342.2 [M+1]$^+$; mp 184-186° C.

Example 25

N1-(3-methyl)-1,2-dihydropyrrole-N5-(3-trifluoromethoxy)phenyl biguanide hydrochloride

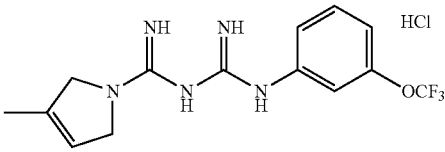 [SMILES: CC1=CCN(C(=N)NC(=N)Nc2cccc(OC(F)(F)F)c2)C1 ; Cl]

$^1$H NMR (600 MHz, CD$_3$OD) δ 7.59 (m, 1H), 7.46 (m, 2H), 7.23 (m, 1H), 5.88 (s, 1H), 4.45 (m, 2H), 4.16 (m, 2H), 1.83 (m, 3H); LC-MS m/z 328.2 [M+1]$^+$; mp 263-265° C.

Example 26

N1-(3-methyl)-1,2-dihydropyrrole-N5-(4-trifluoromethyl)benzyl biguanide hydrochloride

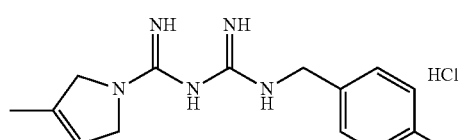

$^1$H NMR (600 MHz, CD$_3$OD) δ 7.74 (m, 1H), 7.64 (m, 2H), 7.51 (m, 1H), 5.56 (s, 1H), 4.48 (s, 2H), 4.19 (m, 4H), 1.83 (m, 3H); LC-MS m/z 326.2 [M+1]$^+$; mp 267-269° C.

Example 27

N1-(3-methyl)-1,2-dihydropyrrole-N5-(4-chloro,3-trifluoromethyl)benzyl biguanide hydrochloride

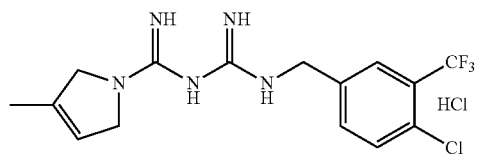 [SMILES: CC1=CCN(C(=N)NC(=N)NCc2ccc(Cl)c(C(F)(F)F)c2)C1 ; Cl]

$^1$H NMR (600 MHz, CD$_3$OD) δ 7.61 (m, 1H), 7.59 (m, 2H), 7.51 (m, 1H), 5.59 (s, 1H), 4.48 (s, 2H), 4.26 (m, 4H), 1.85 (s, 3H); LC-MS m/z 326.2 [M+1]$^+$; mp 230-232° C.

Example 28

N1-1,2,3,6-tetrahydropyridine-N5-(4-trifluoromethoxy)phenyl biguanide hydrochloride

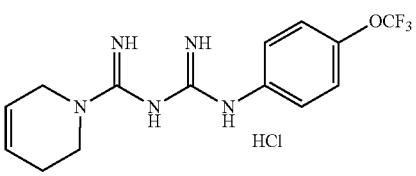 [SMILES: N=C(NC(=N)N1CC=CCC1)Nc1ccc(OC(F)(F)F)cc1 ; Cl]

¹H NMR (600 MHz, CD₃OD) δ 7.46 (d, 2H), 7.24 (d, 2H), 5.95 (m, 1H), 5.74 (m, 1H), 4.00 (s, 2H), 3.64 (t, 2H), 2.23 (s, 2H); LC-MS m/z 328.1 [M+1]⁺

Example 29

N1-1,2,3,6-tetrahydropyridine-N5-(4-trifluoromethyl)phenyl biguanide hydrochloride

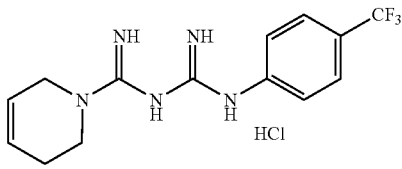 [SMILES: N=C(NC(=N)N1CC=CCC1)Nc1ccc(C(F)(F)F)cc1 ; Cl]

¹H NMR (600 MHz, CD₃OD) δ 7.59 (m, 4H), 5.96 (m, 1H), 5.75 (m, 1H), 4.01 (s, 2H), 3.65 (t, 2H), 2.25 (s, 2H); LC-MS m/z 312.2 [M+1]⁺

Example 30

N1-1,2,3,6-tetrahydropyridine-N5-(3-trifluoromethoxy)phenyl biguanide hydrochloride

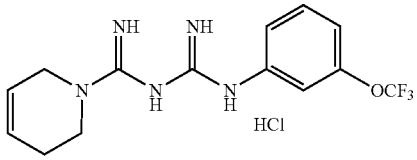 [SMILES: N=C(NC(=N)N1CC=CCC1)Nc1cccc(OC(F)(F)F)c1 ; Cl]

¹H NMR (600 MHz, CD₃OD) δ 7.82 (s, 1H), 7.57 (d, 1H), 7.49 (t, 1H), 7.38 (d, 1H), 5.97 (m, 1H), 5.74 (m, 1H), 4.01 (s, 2H), 3.65 (t, 2H), 2.24 (s, 2H)

Example 31

N1-1,2,3,6-tetrahydropyridine-N5-(3-trifluoromethyl)phenyl biguanide hydrochloride

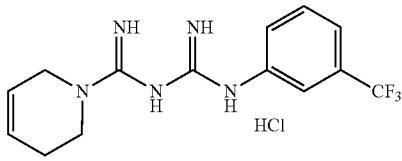 [SMILES: N=C(NC(=N)N1CC=CCC1)Nc1cccc(C(F)(F)F)c1 ; Cl]

¹H NMR (600 MHz, CD₃OD) δ 7.82 (s, 1H), 7.57 (d, 1H), 7.49 (t, 1H), 7.37 (d, 1H), 5.95 (m, 1H), 5.74 (m, 1H), 4.01 (s, 2H), 3.65 (t, 2H), 2.24 (s, 2H); LC-MS m/z 312.2 [M+1]⁺

Example 32

N1-1,2,3,6-tetrahydropyridine-N5-(4-fluoro, 3-trifluoromethyl)phenyl biguanide hydrochloride

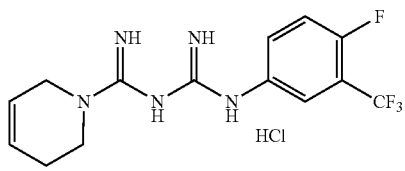 [SMILES: N=C(NC(=N)N1CC=CCC1)Nc1ccc(F)c(C(F)(F)F)c1 ; Cl]

¹H NMR (600 MHz, CD₃OD) δ 7.80 (m, 1H), 7.60 (m, 1H), 7.28 (t, 1H), 5.95 (m, 1H), 5.73 (m, 1H), 4.00 (s, 2H), 3.64 (t, 2H), 2.23 (s, 2H); LC-MS m/z 330.2 [M+1]⁺

Example 33

N1-1,2,3,6-tetrahydropyridine-N5-(4-chloro, 3-trifluoromethyl)phenyl biguanide hydrochloride

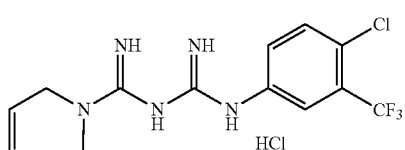

¹H NMR (600 MHz, CD₃OD) δ 7.93 (m, 1H), 7.59 (m, 1H), 7.53 (d, 1H), 5.96 (m, 1H), 5.74 (m, 1H), 4.01 (s, 2H), 3.65 (t, 2H), 2.24 (s, 2H); LC-MS m/z 346.0 [M+1]⁺

Example 34

N1-1,2,3,6-tetrahydropyridine-N5-(3-fluoro, 4-trifluoromethoxy)phenyl biguanide hydrochloride

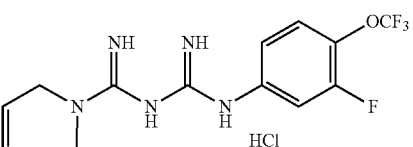

¹H NMR (600 MHz, CD₃OD) δ 7.56 (m, 1H), 7.34 (t, 1H), 7.16 (m, 1H), 5.97 (m, 1H), 5.74 (m, 1H), 4.01 (s, 2H), 3.65 (t, 2H), 2.25 (s, 2H); LC-MS m/z 346.2 [M+1]⁺

Example 35

N1-1,2,3,6-tetrahydropyridine-N5-(4-chloro)phenyl biguanide hydrochloride

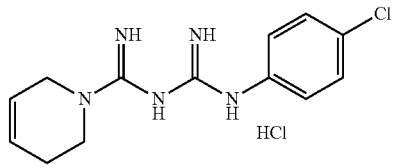 [SMILES: N=C(NC(=N)N1CC=CCC1)Nc1ccc(Cl)cc1 ; Cl]

¹H NMR (600 MHz, CD₃OD) δ 7.37 (d, 2H), 7.31 (d, 2H), 5.97 (m, 1H), 5.74 (m, 1H), 3.99 (s, 2H), 3.63 (t, 2H), 2.23 (s, 2H); LC-MS m/z 278.2 [M+1]⁺

Example 36

N1-1,2,3,6-tetrahydropyridine-N5-(4-bromo)phenyl biguanide hydrochloride

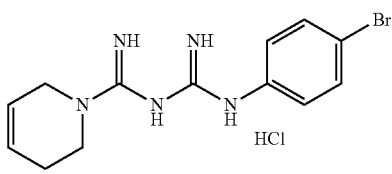 [SMILES: N=C(NC(=N)N1CC=CCC1)Nc1ccc(Br)cc1 ; Cl]

¹H NMR (600 MHz, CD₃OD) δ 7.45 (d, 2H), 7.30 (d, 2H), 5.97 (m, 1H), 5.74 (m, 1H), 3.99 (s, 2H), 3.63 (t, 2H), 2.23 (s, 2H); LC-MS m/z 323.0 [M+1]⁺

Example 37

N1-1,2,3,6-tetrahydropyridine-N5-(4-fluoro)phenyl biguanide hydrochloride

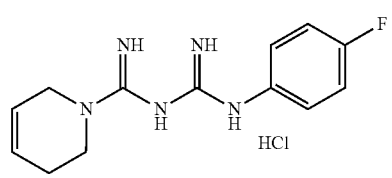 [SMILES: N=C(NC(=N)N1CC=CCC1)Nc1ccc(F)cc1 ; Cl]

¹H NMR (600 MHz, CD₃OD) δ 7.35 (d, 2H), 7.07 (d, 2H), 5.94 (m, 1H), 5.72 (m, 1H), 3.97 (s, 2H), 3.62 (t, 2H), 2.23 (s, 2H); LC-MS m/z 262.2 [M+1]⁺

Example 38

N1-1,2,3,6-tetrahydropyridine-N5-(3,5-dimethoxy)phenyl biguanide hydrochloride

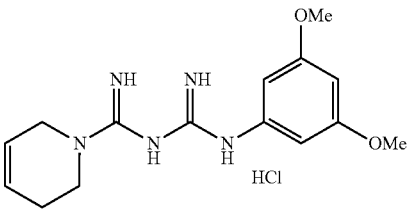 [SMILES: COc1cc(NC(=N)NC(=N)N2CC=CCC2)cc(OC)c1 ; Cl]

¹H NMR (600 MHz, CD₃OD) δ 6.56 (d, 2H), 6.27 (t, 1H), 5.96 (m, 1H), 5.74 (m, 1H), 4.00 (s, 2H), 3.76 (s, 6H), 3.64 (t, 2H), 2.23 (s, 2H); LC-MS m/z 304.2 [M+1]⁺

Example 39

N1-1,2,3,6-tetrahydropyridine-N5-phenyl biguanide hydrochloride

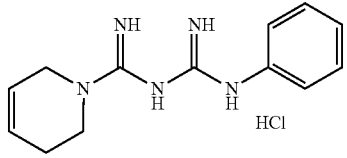 [SMILES: N=C(NC(=N)N1CC=CCC1)Nc1ccccc1 ; Cl]

¹H NMR (600 MHz, CD₃OD) δ 7.33 (m, 4H), 7.13 (m, 1H), 5.94 (m, 1H), 5.73 (m, 1H), 3.98 (s, 2H), 3.63 (t, 2H), 2.22 (s, 2H); LC-MS m/z 244.2 [M+1]⁺

Example 40

N1-1,2,3,6-tetrahydropyridine-N5-(4-methoxyl)phenyl biguanide hydrochloride

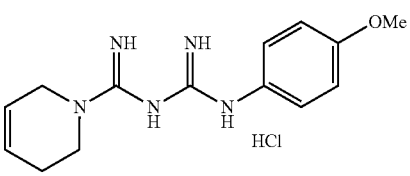 [SMILES: COc1ccc(NC(=N)NC(=N)N2CC=CCC2)cc1 ; Cl]

¹H NMR (600 MHz, CD₃OD) δ 7.23 (d, 2H), 6.91 (d, 2H) 5.93 (m, 1H), 5.72 (m, 1H), 3.96 (s, 2H), 3.78 (s, 3H), 3.61 (t, 2H), 2.21 (s, 2H); LC-MS m/z 274.2 [M+1]⁺

Example 41

N1-1,2,3,6-tetrahydropyridine-N5-(3-methoxyl)phenyl biguanide hydrochloride

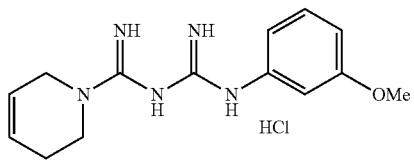 [SMILES: COc1cccc(NC(=N)NC(=N)N2CC=CCC2)c1 ; Cl]

¹H NMR (600 MHz, CD₃OD) δ 7.22 (t, 1H), 7.00 (t, 1H), 6.88 (m, 1H), 6.71 (m, 1H), 5.95 (m, 1H), 5.74 (m, 1H), 3.99 (s, 2H), 3.77 (s, 3H), 3.64 (t, 2H), 2.23 (s, 2H); LC-MS m/z 274.2 [M+1]⁺

Example 42

N1-1,2-dihydropyrrole-N5-(4-methoxyl)phenyl biguanide hydrochloride

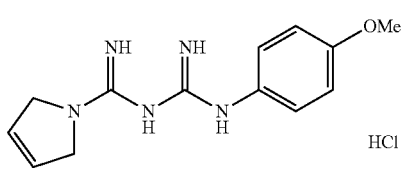 [SMILES: COc1ccc(NC(=N)NC(=N)N2CC=CC2)cc1 ; Cl]

¹H NMR (600 MHz, CD₃OD) δ 7.25 (d, 2H), 6.91 (d, 2H), 5.92 (s, 2H), 4.22 (d, 4H), 3.78 (s, 3H); LC-MS m/z 260.2 [M+1]⁺

Example 43

N1-1,2-dihydropyrrole-N5-(3-methoxyl)phenyl biguanide hydrochloride

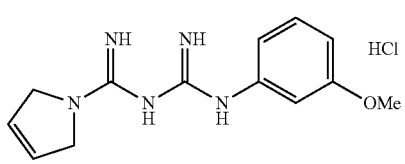 [SMILES: COc1cccc(NC(=N)NC(=N)N2CC=CC2)c1 ; Cl]

¹H NMR (600 MHz, CD₃OD) δ 7.22 (t, 1H), 7.03 (t, 1H), 6.91 (m, 1H), 6.71 (m, 1H), 5.93 (s, 2H), 4.29 (d, 4H), 3.77 (s, 3H); LC-MS m/z 260.2 [M+1]⁺

Example 44

N1-1,2-dihydropyrrole-N5-phenyl biguanide hydrochloride

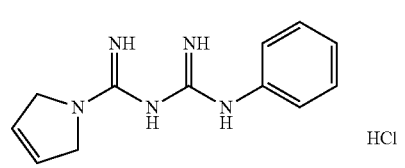 [SMILES: N=C(NC(=N)N1CC=CC1)Nc1ccccc1 ; Cl]

¹H NMR (600 MHz, CD₃OD) δ 7.37 (m, 4H), 7.12 (t, 1H), 5.93 (s, 2H), 4.27 (d, 4H); LC-MS m/z 230.2 [M+1]⁺

Example 45

N1-1,2-dihydropyrrole-N5-(3,5-dimethoxy)phenyl biguanide hydrochloride

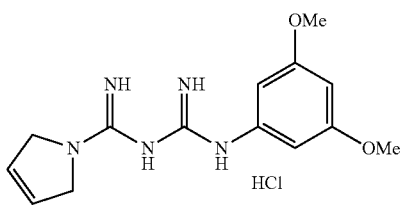 [SMILES: COc1cc(NC(=N)NC(=N)N2CC=CC2)cc(OC)c1 ; Cl]

¹H NMR (600 MHz, CD₃OD) δ 6.58 (d, 2H), 6.27 (t, 1H), 5.93 (m, 1H), 4.30 (d, 4H), 3.75 (s, 6H); LC-MS m/z 290.2 [M+1]⁺

Example 46

N1-1,2-dihydropyrrole-N5-(4-fluoro, 3-trifluoromethyl)phenyl biguanide hydrochloride

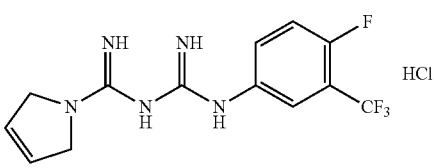 [SMILES: N=C(NC(=N)N1CC=CC1)Nc1ccc(F)c(C(F)(F)F)c1 ; Cl]

¹H NMR (600 MHz, CD₃OD) δ 7.82 (m, 1H), 7.64 (m, 1H), 7.29 (t, 1H), 5.94 (s, 2H), 4.26 (d, 4H); LC-MS m/z 316.2 [M+1]⁺

Example 47

N1-1,2-dihydropyrrole-N5-(3-fluoro, 4-trifluoromethyl)phenyl biguanide hydrochloride

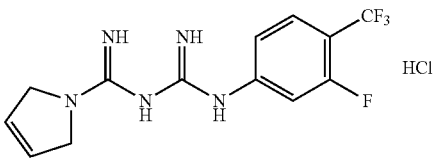 [SMILES: N=C(NC(=N)N1CC=CC1)Nc1ccc(C(F)(F)F)c(F)c1 ; Cl]

¹H NMR (600 MHz, CD₃OD) δ 7.21 (m, 2H), 7.15 (d, 2H), 5.94 (m, 1H), 5.73 (m, 1H), 3.97 (s, 2H), 3.62 (t, 2H), 2.30 (s, 3H), 2.22 (s, 2H); LC-MS m/z 316.2 [M+1]⁺

Example 48

N1-1,2,3,6-tetrahydropyridine-N5-(4-methyl)phenyl biguanide hydrochloride

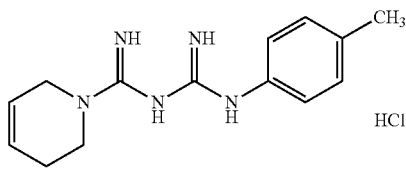 [SMILES: Cc1ccc(NC(=N)NC(=N)N2CC=CCC2)cc1 ; Cl]

¹H NMR (600 MHz, CD₃OD) δ 7.21 (m, 2H), 7.15 (d, 2H), 5.94 (m, 1H), 5.73 (m, 1H), 3.97 (s, 2H), 3.62 (t, 2H), 2.30 (s, 3H), 2.22 (s, 2H); LC-MS m/z 258.2 [M+1]⁺

Example 49

N1-1,2,3,6-tetrahydropyridine-N5-(3-methyl)phenyl biguanide hydrochloride

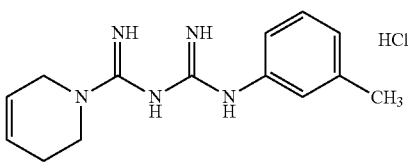 [SMILES: Cc1cccc(NC(=N)NC(=N)N2CC=CCC2)c1 ; Cl]

¹H NMR (600 MHz, CD₃OD) δ 7.21 (m, 3H), 6.96 (d, 2H), 5.95 (m, 1H), 5.73 (m, 1H), 3.98 (s, 2H), 3.63 (t, 2H), 2.32 (s, 3H), 2.22 (s, 2H); LC-MS m/z 258.2 [M+1]⁺

Example 50

N1-1,2-dihydropyrrole-N5-(4-methyl)phenyl biguanide hydrochloride

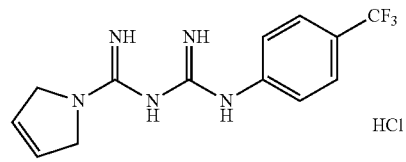 [SMILES: N=C(NC(=N)N1CC=CC1)Nc1ccc(C(F)(F)F)cc1 ; Cl]

¹H NMR (600 MHz, CD₃OD) δ 7.24 (d, 2H), 7.15 (d, 2H), 5.92 (s, 2H), 4.26 (d, 4H), 2.31 (s, 3H); LC-MS m/z 244.2 [M+1]⁺

Example 51

N1-1,2-dihydropyrrole-N5-(3-methyl)phenyl biguanide hydrochloride

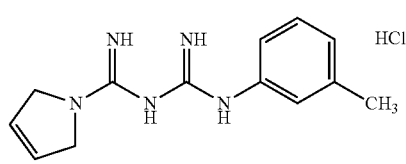 [SMILES: Cc1cccc(NC(=N)NC(=N)N2CC=CC2)c1 ; Cl]

¹H NMR (600 MHz, CD₃OD) δ 7.17 (m, 3H), 6.96 (d, 1H), 5.93 (s, 2H), 4.27 (d, 4H), 2.32 (s, 3H); LC-MS m/z 244.2 [M+1]⁺

Example 52

N1-1,2-dihydropyrrole-N5-(3-trifluoromethoxy)phenyl biguanide hydrochloride

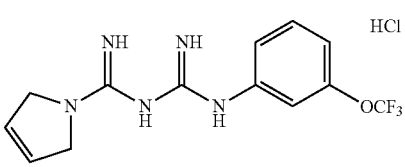 [SMILES: N=C(NC(=N)N1CC=CC1)Nc1cccc(OC(F)(F)F)c1 ; Cl]

¹H NMR (600 MHz, CD₃OD) δ 7.83 (s, 1H), 7.61 (d, 1H), 7.49 (t, 1H), 7.38 (d, 1H), 5.94 (s, 2H), 4.28 (d, 4H)

Example 53

N1-1,2,3,6-tetrahydropyridine-N5-hexyl biguanide hydrochloride

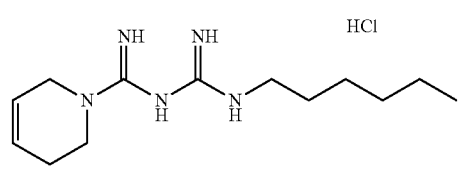 [SMILES: Cl ; CCCCCCNC(=N)NC(=N)N1CC=CCC1]

¹H NMR (600 MHz, CD₃OD) δ 5.93 (m, 1H), 5.72 (m, 1H), 3.98 (m, 2H), 3.63 (t, 2H), 3.20 (t, 2H), 2.23 (t, 2H), 1.70-1.33 (m, 8H), 0.91 (t, 3H); LC-MS m/z 252.4 [M+1]⁺

Example 54

N1-1,2,3,6-tetrahydropyridine-N5-(4-trifluoromethoxy)benzyl biguanide hydrochloride

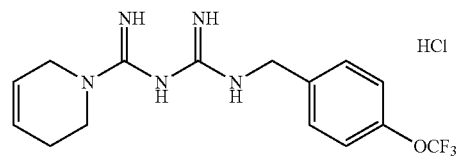 [SMILES: N=C(NCc1ccc(OC(F)(F)F)cc1)NC(=N)N1CC=CCC1 ; Cl]

¹H NMR (600 MHz, CD₃OD) δ 7.43 (d, 2H), 7.25 (d, 2H), 5.91 (m, 1H), 5.68 (m, 1H), 4.43 (s, 2H), 3.90 (m, 2H), 3.52 (t, 2H), 2.16 (s, 2H); LC-MS m/z 342.2 [M+1]⁺

Example 55

N1-1,2,3,6-tetrahydropyridine-N5-(3-trifluoromethoxy)benzyl biguanide hydrochloride

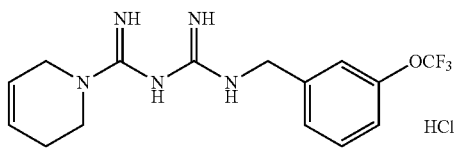 [SMILES: N=C(NCc1cccc(OC(F)(F)F)c1)NC(=N)N1CC=CCC1 ; Cl]

¹H NMR (600 MHz, CD₃OD) δ 7.43 (t, 1H), 7.33 (d, 1H), 7.25 (s, 1H), 7.18 (d, 1H), 5.91 (m, 1H), 5.68 (m, 1H), 4.45 (s, 2H), 3.90 (t, 2H), 3.52 (t, 2H), 2.15 (s, 2H); LC-MS m/z 342.2 [M+1]⁺

Example 56

N1-1,2,3,6-tetrahydropyridine-N5-(4-trifluoromethyl)benzyl biguanide hydrochloride

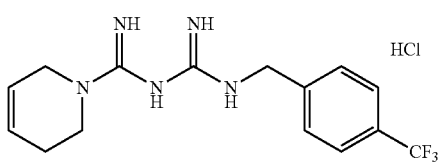 [SMILES: N=C(NCc1ccc(C(F)(F)F)cc1)NC(=N)N1CC=CCC1 ; Cl]

¹H NMR (600 MHz, CD₃OD) δ 7.64 (d, 2H), 7.52 (d, 2H), 5.91 (m, 1H), 5.67 (m, 1H), 4.49 (s, 2H), 3.89 (t, 2H), 3.51 (t, 2H), 2.14 (s, 2H); LC-MS m/z 326.2 [M+1]⁺

Example 57

N1-1,2,3,6-tetrahydropyridine-N5-(3-trifluoromethyl)benzyl biguanide hydrochloride

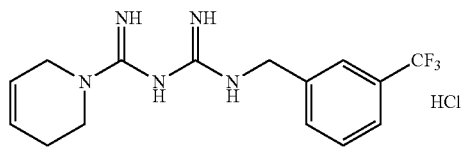 [SMILES: N=C(NCc1cccc(C(F)(F)F)c1)NC(=N)N1CC=CCC1 ; Cl]

¹H NMR (600 MHz, CD₃OD) δ 7.64 (s, 1H), 7.56 (m, 3H), 5.91 (m, 1H), 5.67 (m, 1H), 4.48 (s, 2H), 3.89 (t, 2H), 3.51 (t, 2H), 2.15 (s, 2H); LC-MS m/z 326.2 [M+1]⁺

Example 58

N1-1,2,3,6-tetrahydropyridine-N5-(4-chloro,3-trifluoromethyl)benzyl biguanide hydrochloride

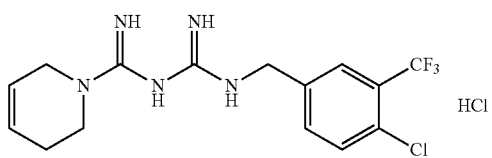 [SMILES: N=C(NCc1ccc(Cl)c(C(F)(F)F)c1)NC(=N)N1CC=CCC1 ; Cl]

¹H NMR (600 MHz, CD₃OD) δ 7.74 (s, 1H), 7.56 (m, 2H), 5.91 (m, 1H), 5.68 (m, 1H), 4.45 (s, 2H), 3.89 (t, 2H), 3.51 (t, 2H), 2.15 (s, 2H); LC-MS m/z 360.2 [M+1]⁺

Example 59

N1-1,2,3,6-tetrahydropyridine-N5-butyl biguanide hydrochloride

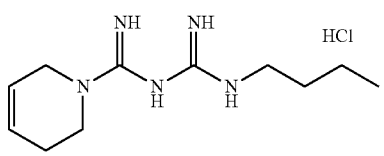 [SMILES: CCCCNC(=N)NC(=N)N1CC=CCC1 ; Cl]

¹H NMR (600 MHz, CD₃OD) δ 5.94 (m, 1H), 5.73 (m, 1H), 4.19 (t, 1H), 3.98 (m, 2H), 3.64 (t, 2H), 3.20 (t, 1H), 2.23 (t, 2H), 1.70-1.37 (m, 4H), 0.95 (m, 3H); LC-MS m/z 224.2 [M+1]⁺

Example 60

N1-1,2,3,6-tetrahydropyridine-N5-propyl biguanide hydrochloride

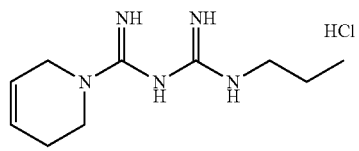

¹H NMR (600 MHz, CD₃OD) δ 5.94 (m, 1H), 5.73 (m, 1H), 3.97 (m, 2H), 3.62 (t, 2H), 3.16 (t, 2H), 2.23 (t, 2H), 1.58 (m, 2H), 0.95 (m, 3H); LC-MS m/z 210.2 [M+1]⁺

Example 61

N1-1,2,3,6-tetrahydropyridine biguanide hydrochloride

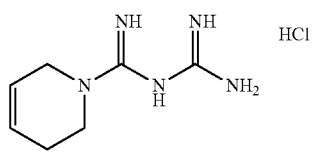 [SMILES: N=C(N)NC(=N)N1CC=CCC1 ; Cl]

¹H NMR (600 MHz, CD₃OD) δ 5.97 (m, 1H), 5.77 (m, 1H), 3.98 (m, 2H), 3.64 (m, 2H), 2.40 (m, 1H), 2.23 (m, 1H); LC-MS m/z 168.2 [M+1]⁺

Example 62

Synthesis of N1-(3-methyl)piperidine cyanoguanidine

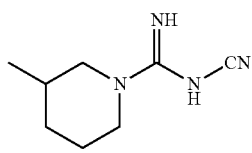

Concentrated hydrochloric acid (0.9 mL, 0.010 mol) was added to a butanol (10 mL) solution containing 3-methylpiperidine (1.00 g, 0.010 mol), and stirred at 0° C. for 30 minutes. Sodium dicyanamide (0.99 g, 0.011 mol) was added to the mixed solution, and the resulting reaction mixture was stirred for 24 hours under reflux.

After completion of the reaction was confirmed, sodium chloride formed by filtering the reaction mixture was removed, and the filtrate was then concentrated at a reduced pressure. Ethyl acetate (10 mL) was then added to the concentrate, and stirred at room temperature for an hour. The formed solid was filtered, and the filtrate was washed with ethyl acetate (2×20 mL). The filtrate was dried at a reduced pressure to obtain a white solid target compound (1.34 g, 80.0%).

$^1$H NMR (600 MHz, CD$_3$OD) δ 3.97 (m, 2H), 2.85 (m, 1H), 2.52 (m, 1H), 1.84-1.45 (m, 4H), 1.17 (m, 1H), 0.92 (d, 3H)

Example 63

Synthesis of N1-(2-methyl)piperidine cyanoguanidine

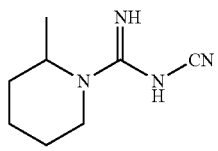

A white solid target compound (1.0 g, 37%) was prepared in the same manner as in Example 62, except that N1-(2-methyl)piperidine was used instead of the N1-(3-methyl)piperidine used in Example 62.

$^1$H NMR (600 MHz, CD$_3$OD) δ 3.98 (m, 2H), 2.85 (m, 1H), 2.53 (m, 1H), 1.82 (m, 1H), 1.71 (m, 1H), 1.59 (m, 1H), 1.48 (m, 1H), 1.91 (s, 3H); LC-MS m/z 167.2 [M+1]$^+$

Example 64

Synthesis of N1-(2,6-dimethyl)piperidine cyanoguanidine

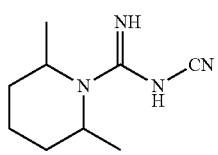

A white solid target compound (0.75 g, 47.2%) was prepared in the same manner as in Example 62, except that N1-(2,6-dimethyl)piperidine was used instead of the N1-(3-methyl)piperidine used in Example 62.

$^1$H NMR (600 MHz, CD$_3$OD) δ 4.31 (s, 2H), 1.85 (m, 1H), 1.70 (m, 4H), 1.50 (m, 1H), 1.48 (d, 6H); LC-MS m/z 181.2 [M+1]$^+$

Example 65

N1-(3-methyl)piperidine-N5-(3-trifluoromethyl) benzyl biguanide hydrochloride

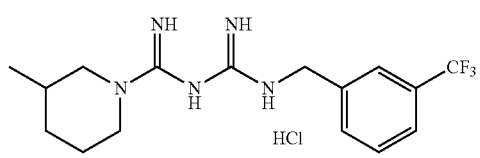 [SMILES: CC1CCCN(C(=N)NC(=N)NCc2cccc(C(F)(F)F)c2)C1 ; Cl]

Concentrated hydrochloric acid (0.24 mL, 2.71 mmol) was added to a butanol (10 mL) solution containing (3-trifluoromethyl)benzylamine (0.28 mL, 1.99 mmol) at room temperature, and then stirred for 30 minutes. The N1-(3-methyl)piperidine cyanoguanidine (300 mg, 1.81 mmol) obtained in Example 1 was added to the reaction mixture, and then stirred for 2 hours under reflux. The reaction mixture was concentrated at a reduced pressure, and ethyl acetate (3 mL) was added to the concentrated reaction mixture. The formed solid was filtered, and the filtrate was then dried at a reduced pressure to obtain a white solid target compound (0.37 g, 54.7%).

$^1$H NMR (600 MHz, CD$_3$OD) δ 7.63 (m, 1H), 7.55 (m, 3H), 4.47 (s, 2H), 3.85 (dd, 2H), 2.86 (t, 1H), 2.54 (m, 1H), 1.80 (m, 1H), 1.67 (m, 1H), 1.56 (m, 1H), 1.47 (m, 1H), 1.17 (q, 1H), 0.85 (d, 3H); LC-MS m/z 342.2 [M+1]$^+$

Target compounds of the following Examples 66 to 98 were prepared in the same manner as in Example 65, except that the cyanoguanidine and amine compounds synthesized in Examples 63 and 64, which corresponded to the target compounds, were used respectively instead of the N1-(3-methyl)piperidine cyanoguanidine synthesized in Example 62 and the (3-trifluoromethyl)benzylamine used in Example 65.

Example 66

N1-(3-methyl)piperidine-N5-(4-chloro)benzyl biguanide hydrochloride

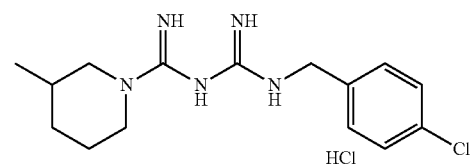 [SMILES: CC1CCCN(C(=N)NC(=N)NCc2ccc(Cl)cc2)C1 ; Cl]

$^1$H NMR (600 MHz, CD$_3$OD) δ 7.28 (m, 4H), 4.29 (m, 2H), 3.82 (m, 2H), 2.81 (m, 1H), 2.51 (m, 1H), 1.57 (m, 4H), 1.15 (m, 1H) 0.84 (m, 3H); LC-MS m/z 308.2 [M+1]$^+$; mp 256-258° C.

Example 67

N1-(3-methyl)piperidine-N5-(4-fluoro)phenyl biguanide hydrochloride

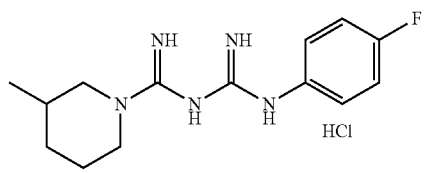 [SMILES: CC1CCCN(C(=N)NC(=N)Nc2ccc(F)cc2)C1 ; Cl]

$^1$H NMR (600 MHz, CD$_3$OD) δ 7.40 (m, 4H), 4.29 (m, 2H), 3.89 (m, 2H), 2.94 (m, 1H), 2.67 (m, 1H), 1.70 (m, 4H), 1.18 (m, 1H) 0.87 (m, 3H); LC-MS m/z 278.2 [M+1]$^+$; mp 265-267° C.

Example 68

N1-(3-methyl)piperidine-N5-(4-bromo)phenyl biguanide hydrochloride

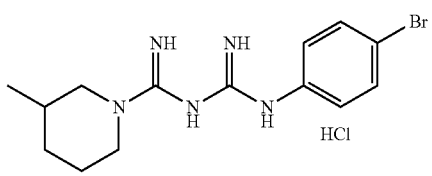 [SMILES: CC1CCCN(C(=N)NC(=N)Nc2ccc(Br)cc2)C1 ; Cl]

$^1$H NMR (600 MHz, CD$_3$OD) δ 7.36 (m, 2H), 7.06 (m, 2H), 3.89 (m, 2H), 2.89 (m, 1H), 2.61 (m, 1H), 1.66 (m, 4H), 1.17 (m, 1H), 0.86 (m, 3H); LC-MS m/z 339.2 [M+1]$^+$; mp 252-254° C.

Example 69

N1-(3-methyl)piperidine-N5-(4-chloro, 3-trifluoromethyl)phenyl biguanide hydrochloride

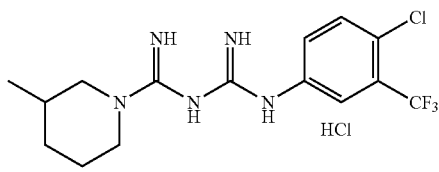 [SMILES: CC1CCCN(C(=N)NC(=N)Nc2ccc(Cl)c(C(F)(F)F)c2)C1 ; Cl]

$^1$H NMR (600 MHz, CD$_3$OD) δ 7.93 (m, 1H), 7.51 (m, 2H), 3.92 (m, 2H), 2.99 (m, 1H), 2.69 (m, 1H), 1.86 (m, 1H), 1.73 (m, 2H), 1.56 (m, 1H), 1.20 (m, 1H), 0.91 (m, 3H); LC-MS m/z 362.2 [M+1]$^+$; mp 230-232° C.

Example 70

N1-(3-methyl)piperidine-N5-(3-fluoro, 4-trifluoromethyl)phenyl biguanide hydrochloride

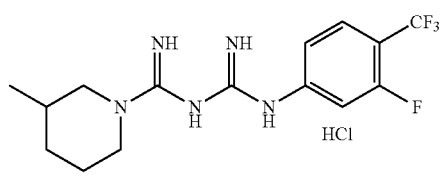 [SMILES: CC1CCCN(C(=N)NC(=N)Nc2ccc(C(F)(F)F)c(F)c2)C1 ; Cl]

$^1$H NMR (600 MHz, CD$_3$OD) δ 7.57 (m, 2H), 7.21 (m, 1H), 3.92 (m, 2H), 3.00 (m, 1H), 2.72 (m, 1H), 1.88 (m, 1H), 1.71 (m, 3H), 1.24 (m, 1H), 0.91 (m, 3H); LC-MS m/z 346.2 [M+1]$^+$; mp 228-230° C.

Example 71

N1-(3-methyl)piperidine-N5-(4-fluoro, 3-trifluoromethyl)phenyl biguanide hydrochloride

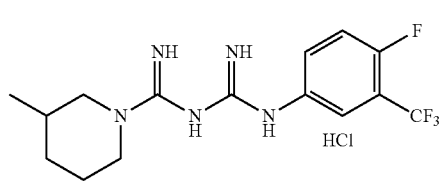 [SMILES: CC1CCCN(C(=N)NC(=N)Nc2ccc(F)c(C(F)(F)F)c2)C1 ; Cl]

$^1$H NMR (600 MHz, CD$_3$OD) δ 7.85 (m, 2H), 7.60 (m, 1H), 7.29 (t, J=9.6 Hz, 1H), 3.93 (m, 2H), 3.02 (m, 1H), 2.70 (m, 1H), 1.88 (m, 1H), 1.77 (m, 2H), 1.58 (m, 1H), 1.25 (m, 1H), 0.95 (m, 3H); LC-MS m/z 346.2 [M+1]$^+$; mp 243-245° C.

Example 72

N1-(2-methyl)piperidine-N5-(4-trifluoromethoxy)phenyl biguanide hydrochloride

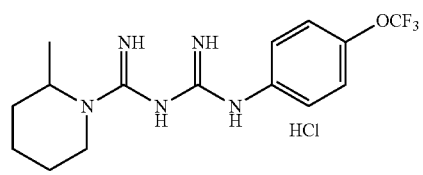 [SMILES: CC1CCCCN1C(=N)NC(=N)Nc1ccc(OC(F)(F)F)cc1 ; Cl]

$^1$H NMR (600 MHz, CD$_3$OD) δ 7.42 (m, 2H), 7.20 (m, 2H), 4.35 (m, 1H), 3.88 (m, 1H), 3.06 (m, 1H), 1.71 (m, 3H), 1.59 (m, 2H), 1.48 (m, 1H), 1.22 (s, 3H); LC-MS m/z 344.2 [M+1]$^+$; mp 250-252° C.

Example 73

N1-(2-methyl)piperidine-N5-(3-trifluoromethoxy) phenyl biguanide hydrochloride

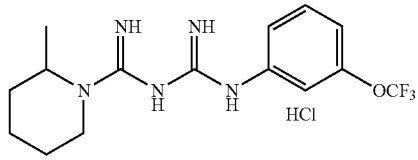 [SMILES: CC1CCCCN1C(=N)NC(=N)Nc1cccc(OC(F)(F)F)c1 ; Cl]

$^1$H NMR (600 MHz, CD$_3$OD) δ 7.52 (m, 1H), 7.37 (m, 1H), 7.25 (m, 1H), 6.96 (m, 1H), 4.41 (m, 1H), 3.91 (m, 1H), 3.13 (m, 1H), 1.74 (m, 3H), 1.64 (m, 2H), 1.51 (m, 1H) 1.26 (m, 3H); LC-MS m/z 344.2 [M+1]$^+$; mp 246-248° C.

Example 74

N1-(2-methyl)piperidine-N5-(4-trifluoromethyl) phenyl biguanide hydrochloride

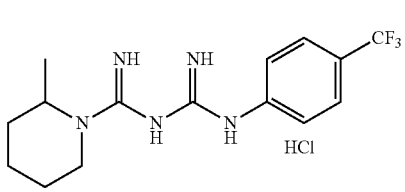 [SMILES: CC1CCCCN1C(=N)NC(=N)Nc1ccc(C(F)(F)F)cc1 ; Cl]

$^1$H NMR (600 MHz, CD$_3$OD) δ 7.56 (m, 4H), 4.37 (m, 1H), 3.91 (m, 1H), 3.12 (m, 1H), 1.73 (m, 3H), 1.61 (m, 2H), 1.52 (m, 1H) 1.24 (m, 3H); LC-MS m/z 329.2 [M+1]$^+$; mp 252-254° C.

Example 75

N1-(3-methyl)piperidine-N5-(3-fluoro, 4-trifluoromethoxy)phenyl biguanide hydrochloride

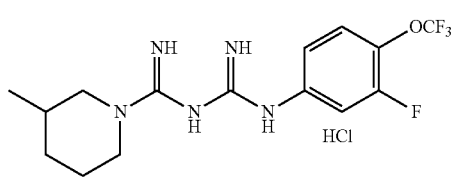 [SMILES: CC1CCCN(C(=N)NC(=N)Nc2ccc(OC(F)(F)F)c(F)c2)C1 ; Cl]

$^1$H NMR (600 MHz, CD$_3$OD) δ 7.50 (m, 1H), 7.23 (m, 1H), 7.08 (m, 1H), 2.85 (m, 2H), 2.63 (m, 1H), 1.79 (m, 1H), 1.67 (m, 3H), 1.58 (m, 1H), 1.17 (m, 1H), 0.86 (m, 3H); LC-MS m/z 362.2 [M+1]$^+$; mp 243-245° C.

Example 76

N1-(2-methyl)piperidine-N5-(3-fluoro, 4-trifluoromethoxy)phenyl biguanide hydrochloride

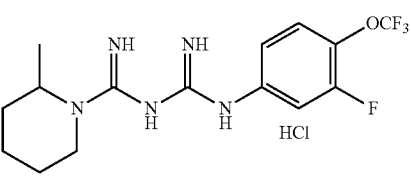 [SMILES: CC1CCCCN1C(=N)NC(=N)Nc1ccc(OC(F)(F)F)c(F)c1 ; Cl]

$^1$H NMR (600 MHz, CD$_3$OD) δ 7.58 (m, 1H), 7.36 (m, 1H), 7.16 (m, 1H), 4.41 (m, 1H), 3.92 (m, 1H), 3.16 (m, 1H), 1.70 (m, 6H) 1.29 (m, 3H); LC-MS m/z 362.0 [M+1]$^+$; mp 241-243° C.

Example 77

N1-(2-methyl)piperidine-N5-(4-chloro)phenyl biguanide hydrochloride

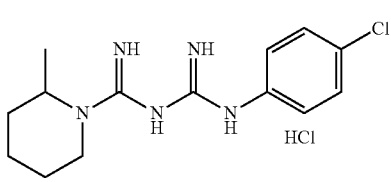 [SMILES: CC1CCCCN1C(=N)NC(=N)Nc1ccc(Cl)cc1 ; Cl]

$^1$H NMR (600 MHz, CD$_3$OD) δ 7.30 (m, 4H), 4.36 (m, 1H), 3.89 (m, 1H), 3.10 (m, 1H), 1.61 (m, 5H), 1.49 (m, 1H), 1.25 (m, 3H); LC-MS m/z 294.0 [M+1]$^+$; mp 251-253° C.

Example 78

N1-(2-methyl)piperidine-N5-(4-fluoro, 3-trifluoromethyl)phenyl biguanide hydrochloride

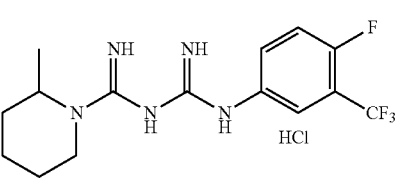

$^1$H NMR (600 MHz, CD$_3$OD) δ 7.84 (m, 1H), 7.56 (m, 1H), 7.28 (m, 1H), 4.39 (m, 1H), 3.90 (m, 1H), 3.13 (m, 1H), 1.73 (m, 5H), 1.51 (m, 1H), 1.25 (m, 3H); LC-MS m/z 346.0 [M+1]$^+$; mp 251-253° C.

Example 79

N1-(2-methyl)piperidine-N5-(3-trifluoromethyl)phenyl biguanide hydrochloride

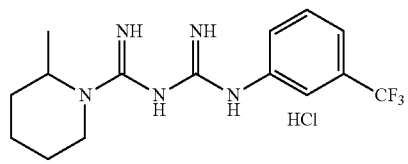

$^1$H NMR (600 MHz, CD$_3$OD) δ 7.83 (m, 1H), 7.48 (m, 2H), 7.32 (m, 1H), 4.39 (m, 1H), 3.92 (m, 1H), 3.13 (m, 1H), 1.73 (m, 6H), 1.20 (m, 3H); LC-MS m/z 328.2 [M+1]$^+$; mp 249-251° C.

Example 80

N1-(2-methyl)piperidine-N5-(4-chloro,3-trifluoromethyl)phenyl biguanide hydrochloride

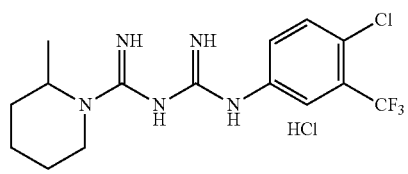 [SMILES: CC1CCCCN1C(=N)NC(=N)Nc1ccc(F)c(C(F)(F)F)c1 ; Cl]

$^1$H NMR (600 MHz, CD$_3$OD) δ 7.83 (m, 1H), 7.95 (m, 1H), 7.51 (m, 2H), 4.38 (m, 1H), 3.91 (m, 1H), 3.12 (m, 1H), 1.60 (m, 6H), 1.20 (m, 3H); LC-MS m/z 362.3 [M+1]$^+$; mp 316-318° C.

Example 81

N1-(3-methyl)piperidine-N5-(4-trifluoromethyl)phenyl biguanide hydrochloride

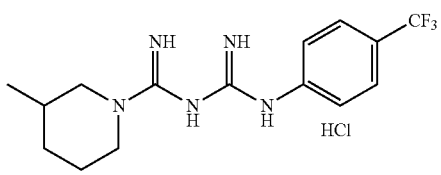 [SMILES: CC1CCCN(C(=N)NC(=N)Nc2ccc(C(F)(F)F)cc2)C1 ; Cl]

$^1$H NMR (600 MHz, CD$_3$OD) δ 7.61 (s, 4H), 3.98 (d, 2H), 3.04 (t, 1H), 2.74 (t, 1H), 1.91 (m, 1H), 1.81-1.73 (m, 2H), 1.63 (m, 1H), 1.27 (q, 1H), 0.98 (d, 3H); LC-MS m/z 328.2 [M+1]$^+$

Example 82

N1-(3-methyl)piperidine-N5-(4-trifluoromethoxy)phenyl biguanide hydrochloride

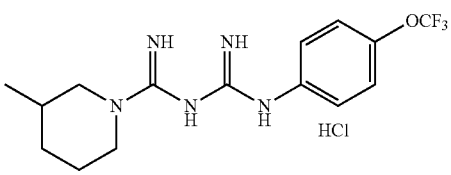 [SMILES: CC1CCCN(C(=N)NC(=N)Nc2ccc(OC(F)(F)F)cc2)C1 ; Cl]

$^1$H NMR (600 MHz, CD$_3$OD) δ 7.46 (m, 2H), 7.22 (m, 2H), 3.94 (d, 2H), 2.97 (t, 1H), 2.67 (t, 1H), 1.86 (m, 1H), 1.76-1.66 (m, 2H), 1.55 (m, 1H), 1.23 (q, 1H), 0.93 (d, 3H); LC-MS m/z 344.2 [M+1]$^+$

Example 83

N1-(3-methyl)piperidine-N5-(3-trifluoromethoxy)phenyl biguanide hydrochloride

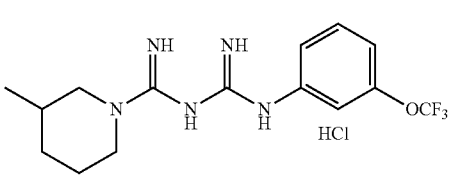 [SMILES: CC1CCCN(C(=N)NC(=N)Nc2cccc(OC(F)(F)F)c2)C1 ; Cl]

$^1$H NMR (600 MHz, CD$_3$OD) δ 7.54 (s, 1H), 7.38 (t, 1H), 7.26 (d, 1H), 6.98 (d, 1H), 3.97 (s, 2H), 3.00 (s, 1H), 2.70 (t, 1H), 1.88 (m, 1H), 1.78-1.71 (m, 2H), 1.59 (m, 1H), 1.24 (q, 1H), 0.91 (d, 3H); LC-MS m/z 344.2 [M+1]$^+$

Example 84

N1-(3-methyl)piperidine-N5-(4-trifluoromethoxy)benzyl biguanide hydrochloride

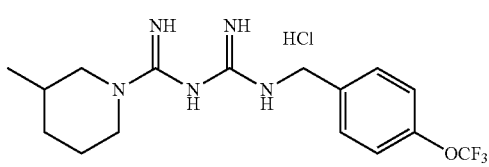 [SMILES: CC1CCCN(C(=N)NC(=N)NCc2ccc(OC(F)(F)F)cc2)C1 ; Cl]

$^1$H NMR (600 MHz, CD$_3$OD) δ 7.42 (d, 2H), 7.25 (d, 2H), 4.41 (s, 2H), 3.84 (dd, 2H), 2.85 (t, 1H), 2.52 (t, 1H), 1.82 (m, 1H), 1.66-1.55 (m, 2H), 1.47 (m, 1H), 1.16 (q, 1H), 0.84 (d, 3H); LC-MS m/z 358.2 [M+1]$^+$

Example 85

N1-(3-methyl)piperidine-N5-(4-fluoro, 3-trifluoromethyl)phenyl biguanide hydrochloride

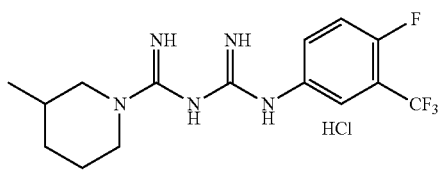 [SMILES: CC1CCCN(C(=N)NC(=N)Nc2ccc(F)c(C(F)(F)F)c2)C1 ; Cl]

$^1$H NMR (600 MHz, CD$_3$OD) δ 7.84 (dd, 1H), 7.58 (dt, 1H), 7.29 (t, 1H), 3.95 (s, 2H), 2.99 (s, 1H), 2.96 (t, 1H), 1.88 (m, 1H), 1.77 (m, 1H), 1.69 (m, 1H), 1.57 (m, 1H), 1.24 (q, 1H), 0.94 (d, 3H); LC-MS m/z 346.2 [M+1]$^+$

Example 86

N1-(3-methyl)piperidine-N5-(4-trifluoromethyl)benzyl biguanide hydrochloride

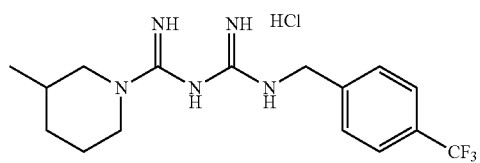 [SMILES: Cl ; CC1CCCN(C(=N)NC(=N)NCc2ccc(C(F)(F)F)cc2)C1]

$^1$H NMR (600 MHz, CD$_3$OD) δ 7.64 (d, 2H), 7.51 (d, 2H), 4.47 (s, 2H), 3.84 (dd, 2H), 2.85 (t, 1H), 2.52 (t, 1H), 1.82 (m, 1H), 1.66 (m, 1H), 1.55 (m, 1H), 1.47 (m, 1H), 1.17 (q, 1H), 0.84 (d, 3H); LC-MS m/z 342.2 [M+1]$^+$

Example 87

N1-(3-methyl)piperidine-N5-(4-chloro)phenyl biguanide hydrochloride

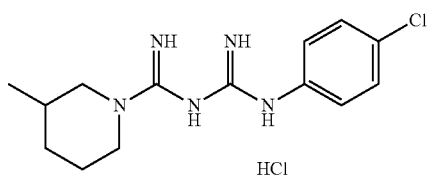 [SMILES: CC1CCCN(C(=N)NC(=N)Nc2ccc(Cl)cc2)C1 ; Cl]

$^1$H NMR (600 MHz, CD$_3$OD) δ 7.35 (m, 4H), 3.96 (m, 2H), 3.00 (m, 1H), 2.67 (m, 1H), 1.89 (m, 1H), 1.68 (m, 3H) 1.24 (m, 1H), 0.94 (m, 3H); LC-MS m/z 294.2 [M+1]$^+$; mp 252-254° C.

Example 88

N1-(3-methyl)piperidine-N5-(3-trifluoromethyl)phenyl biguanide hydrochloride

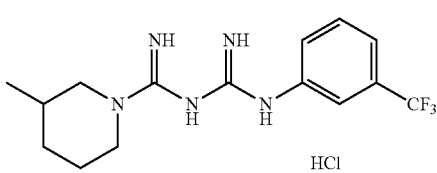 [SMILES: CC1CCCN(C(=N)NC(=N)Nc2cccc(C(F)(F)F)c2)C1 ; Cl]

$^1$H NMR (600 MHz, CD$_3$OD) δ 7.86 (m, 1H), 7.55 (d, 1H), 7.48 t, 1H), 7.37 (d, 1H), 3.97 (s, 2H), 3.01 (t, 1H), 2.71 (t, 1H), 1.89 (m, 1H), 1.77 (m, 1H), 1.70 (m, 1H), 1.59 (m, 1H), 1.25 (q, 1H), 0.94 (d, 3H); LC-MS m/z 328.2 [M+1]$^+$

Example 89

N1-(2,6-dimethyl)piperidine-N5-(4-trifluoromethoxy)phenyl biguanide hydrochloride

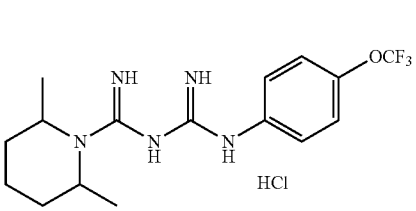 [SMILES: CC1CCCC(C)N1C(=N)NC(=N)Nc1ccc(OC(F)(F)F)cc1 ; Cl]

$^1$H NMR (600 MHz, CD$_3$OD) δ 7.46 (d, 2H), 7.23 (d, 2H), 4.60-4.10 (br s, 2H), 1.90-1.51 (m, 6H), 1.30 (s, 6H); LC-MS m/z 358.4 [M+1]$^+$

Example 90

N1-(2,6-dimethyl)piperidine-N5-(3-trifluoromethoxy)phenyl biguanide hydrochloride

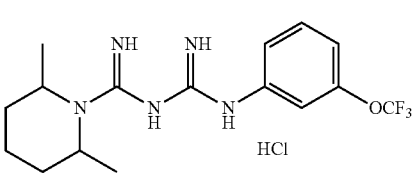 [SMILES: CC1CCCC(C)N1C(=N)NC(=N)Nc1cccc(OC(F)(F)F)c1 ; Cl]

$^1$H NMR (600 MHz, CD$_3$OD) δ 7.54 (s, 1H), 7.37 (t, 1H), 7.25 (d, 1H), 6.97 (d, 1H), 4.60-4.10 (br s, 2H), 1.91-1.52 (m, 6H), 1.31 (s, 6H); LC-MS m/z 358.4 [M+1]$^+$

Example 91

N1-(2,6-dimethyl)piperidine-N5-(4-trifluoromethyl)phenyl biguanide hydrochloride

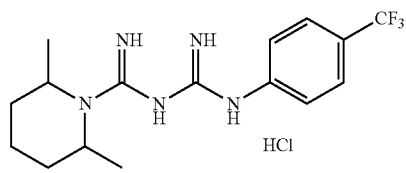 [SMILES: CC1CCCC(C)N1C(=N)NC(=N)Nc1ccc(C(F)(F)F)cc1 ; Cl]

¹H NMR (600 MHz, CD₃OD) δ 7.58 (s, 4H), 4.60-4.10 (br s, 2H), 1.93-1.52 (m, 6H), 1.32 (s, 6H); LC-MS m/z 342.4 [M+1]⁺

Example 92

N1-(2,6-dimethyl)piperidine-N5-(3-trifluoromethyl)phenyl biguanide hydrochloride

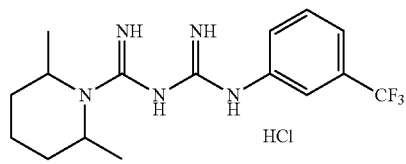 [SMILES: CC1CCCC(C)N1C(=N)NC(=N)Nc1cccc(C(F)(F)F)c1 ; Cl]

¹H NMR (600 MHz, CD₃OD) δ 7.87 (s, 1H), 7.54 (d, 1H), 7.48 (t, 1H), 7.36 (d, 1H), 4.60-4.10 (br s, 2H), 1.93-1.52 (m, 6H), 1.37 (s, 6H); LC-MS m/z 342.4 [M+1]⁺

Example 93

N1-(2,6-dimethyl)piperidine-N5-(4-fluoro,3-trifluoromethyl)phenyl biguanide hydrochloride

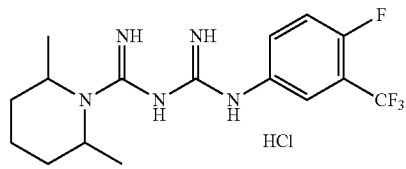 [SMILES: CC1CCCC(C)N1C(=N)NC(=N)Nc1ccc(F)c(C(F)(F)F)c1 ; Cl]

¹H NMR (600 MHz, CD₃OD) δ 7.83 (d, 1H), 7.57 (m, 1H), 7.28 (t, 1H), 4.60-4.10 (br s, 2H), 1.93-1.51 (m, 6H), 1.30 (s, 6H); LC-MS m/z 360.4 [M+1]⁺

Example 94

N1-(2,6-dimethyl)piperidine-N5-(4-chloro,3-trifluoromethyl)phenyl biguanide hydrochloride

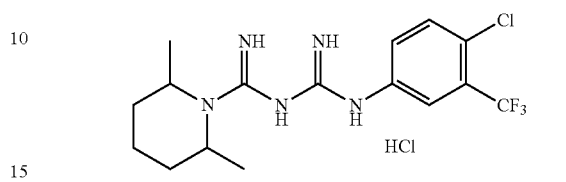

¹H NMR (600 MHz, CD₃OD) δ 7.96 (s, 1H), 7.54 (m, 2H), 4.60-4.10 (br s, 2H), 1.93-1.52 (m, 6H), 1.31 (s, 6H); LC-MS m/z 376.4 [M+1]⁺

Example 95

N1-(2,6-dimethyl)piperidine-N5-(3-fluoro,4-trifluoromethoxy)phenyl biguanide

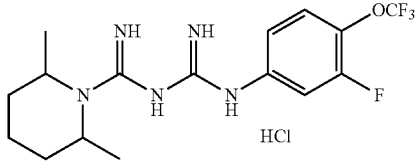 [SMILES: CC1CCCC(C)N1C(=N)NC(=N)Nc1ccc(OC(F)(F)F)c(F)c1 ; Cl]

¹H NMR (600 MHz, CD₃OD) δ 7.56 (d, 1H), 7.33 (t, 1H), 7.15 (d, 1H), 4.60-4.10 (br s, 2H), 1.93-1.52 (m, 6H), 1.32 (s, 6H); LC-MS m/z 376.4 [M+1]⁺

Example 96

N1-(2,6-dimethyl)piperidine-N5-(4-chloro)phenyl biguanide hydrochloride

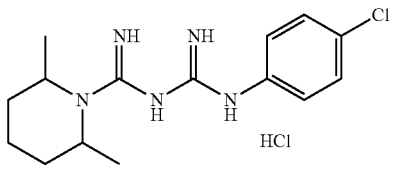 [SMILES: CC1CCCC(C)N1C(=N)NC(=N)Nc1ccc(Cl)cc1 ; Cl]

¹H NMR (600 MHz, CD₃OD) δ 7.36 (m, 2H), 7.30 (m, 2H), 4.60-4.10 (br s, 2H), 1.92-1.51 (m, 6H), 1.30 (s, 6H); LC-MS m/z 308.2, 310.2 [M+1]⁺

Example 97

N1-(2,6-dimethyl)piperidine-N5-(4-bromo)phenyl biguanide hydrochloride

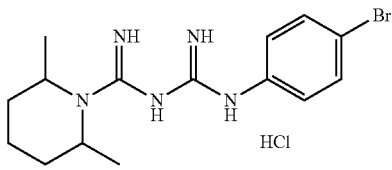 [SMILES: CC1CCCC(C)N1C(=N)NC(=N)Nc1ccc(Br)cc1 ; Cl]

$^1$H NMR (600 MHz, CD$_3$OD) δ 7.45 (d, 2H), 7.31 (d, 2H), 4.60-4.10 (br s, 2H), 1.93-1.51 (m, 6H), 1.30 (s, 6H); LC-MS m/z 353.2 [M+1]$^+$

Example 98

N1-(2,6-dimethyl)piperidine-N5-(4-fluoro)phenyl biguanide hydrochloride

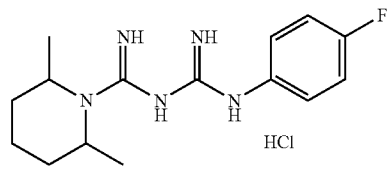 [SMILES: CC1CCCC(C)N1C(=N)NC(=N)Nc1ccc(F)cc1 ; Cl]

$^1$H NMR (600 MHz, CD$_3$OD) δ 7.37 (m, 2H), 7.05 (m, 2H), 4.60-4.10 (br s, 2H), 1.88-1.50 (m, 6H), 1.29 (s, 6H); LC-MS m/z 292.1 [M+1]$^+$

EXPERIMENTAL EXAMPLES

The compounds synthesized by the methods described in the examples of the present invention were evaluated for effects of AMPK activation and inhibition of cancer cell proliferation according to methods described in the following Experimental Examples.

Experimental Example 1

Measurement of AMPK Activation Effect

MCF7 cells derived from human breast cancer cells (purchased from the Korean Cell Line Bank (KCLB)) were used, and AMPK activation effects of the biguanide derivatives were confirmed using an AMPK [pT172] ELISA kit (Invitrogen, Catalog No. KH00651).

MCF7 cells were cultured in a DMEM medium supplemented with 10% fatal bovine serum (commercially available from Gibco Life Technologies (US)). Thereafter, the cultured MCF7 cells were put into a 6-well plate with approximately 5×10$^5$ cells per well, and cultured in an incubator supplied with 5% CO$_2$. Culture media were treated with the derivatives synthesized in the Examples at concentrations of 5, 10 and 50 uM, and then cultured for 24 hours. Metformin was used as the control, and the culture media were treated with 0.05, 0.5, 1, 2, 5 and 10 mM metformin and then tested in the same manner as described for the derivatives synthesized in the Examples. Subsequently, the cells were lysed according to a method presented in the operation manual of the AMPK [pT172] ELISA kit, and 20 µg of a cell lysate was then yielded through protein assay. Thereafter, the AMPK activation effect was obtained by determining a degree of phosphorylation of a 172$^{nd}$ threonine residue (Thr172) of the AMPKα from the cell lysate according to the method presented in the operation manual of the AMPK [pT172] ELISA kit. A degree of AMPK activation by the biguanide derivatives was exhibited as a degree of AMPKα phosphorylation in cells cultured in the presence of the compounds synthesized in the Examples with respect to a degree of AMPKα phosphorylation in cells cultured without treatment with the biguanide derivatives. A curve graph showing AMPK activation according to the concentration of the treated compounds was plotted based on the obtained AMPK activation results, and a concentration (activation concentration 150, AC150) value of a compound whose AMPK activation reached 150% was calculated using a GraphPad Prism 5.0 program. Similarly, degrees of AMPK activation when the concentrations of the treated biguanide derivatives of Examples 4 to 61 were 10 µM and 50 µM are listed in the following Table 1, and degrees of AMPK activation when the concentrations of the treated biguanide derivatives of Examples 65 to 98 were 5 µM to 10 µM are listed in the following Table 2. Some of the compounds were not measurable for AMPK activation due to cytotoxicity when the concentrations of the treated compounds were 50 µM.

TABLE 1

| | AMPK activation effect (%) | | |
|---|---|---|---|
| Example | AC150 (µM) | 10 µM | 50 µM |
| Metformin | 188.3 | ND | 130 |
| 4 | 5.0 | 201 | 584 |
| 5 | 2.8 | 235 | 223 |
| 6 | >50 | 124 | 136 |
| 7 | >50 | 94 | 109 |
| 8 | 8.3 | 139 | 515 |
| 9 | 9.0 | 169 | 371 |
| 10 | 1.4 | 408 | — |
| 11 | 1.4 | 637 | — |
| 12 | 13.8 | 97 | 357 |
| 13 | 9.0 | 135 | 462 |
| 14 | 8.4 | 151 | 507 |
| 15 | 1.6 | 554 | — |
| 16 | 1.7 | 398 | — |
| 17 | 4.7 | 208 | — |
| 18 | 0.81 | — | — |
| 19 | 1.5 | 306 | — |
| 20 | 38.3 | 83 | 172 |
| 21 | 11.9 | 156 | — |
| 22 | 24.5 | 116 | 209 |
| 23 | 21.3 | 57 | 279 |
| 24 | 5.3 | 200 | 421 |
| 25 | 2.2 | 376 | — |
| 26 | 0.68 | 443 | 358 |
| 27 | 13.5 | 119 | 316 |
| 28 | 0.15 | 732 | — |
| 29 | 1.3 | 551 | — |
| 30 | 0.53 | 703 | — |
| 31 | 1.8 | 391 | — |
| 32 | 0.62 | 837 | — |
| 33 | 0.79 | 992 | — |
| 34 | 0.29 | 925 | — |
| 35 | 2.4 | 314 | — |
| 36 | 0.87 | 568 | — |
| 37 | 4.2 | 187 | 522 |
| 38 | >50 | 97 | 117 |
| 39 | 67.2 | 96 | 138 |
| 40 | 37.8 | 122 | 163 |
| 41 | 22.4 | 125 | 201 |
| 42 | 14.7 | 157 | 210 |
| 43 | 4.7 | 200 | 466 |

TABLE 1-continued

| Example | AC150 (μM) | AMPK activation effect (%) 10 μM | 50 μM |
|---|---|---|---|
| 44 | 1.7 | 289 | 577 |
| 45 | 4.8 | 202 | 299 |
| 46 | 1.6 | 448 | — |
| 47 | 1.0 | 758 | — |
| 48 | 4.9 | 178 | 691 |
| 49 | 1.9 | 319 | 917 |
| 50 | 1.4 | 317 | 440 |
| 51 | 3.1 | 241 | 409 |
| 52 | 2.7 | 352 | — |
| 53 | 2.3 | 311 | 589 |
| 54 | 0.87 | 545 | 650 |
| 55 | 2.1 | 389 | 608 |
| 56 | 2.1 | 389 | 671 |
| 57 | 2.7 | 279 | 579 |
| 58 | 1.8 | 500 | — |
| 59 | 16.6 | 104 | 283 |
| 60 | 12.4 | 108 | 338 |
| 61 | >50 | 123 | 132 |

TABLE 2

| Example | AC150 (μM) | AMPK activation effect (%) 5 μM | 10 μM |
|---|---|---|---|
| Metformin | 188.3 | | 130 (at 50 μM) |
| 65 | 2.8 | 147 | 274 |
| 66 | 6.2 | 101 | 204 |
| 67 | 1.6 | 258 | 427 |
| 68 | 13.7 | 52 | 136 |
| 69 | 1.2 | 307 | 650 |
| 70 | 0.9 | 365 | 602 |
| 71 | 1.6 | 259 | 430 |
| 72 | 2.0 | 210 | 386 |
| 73 | 2.0 | 215 | 384 |
| 74 | 2.0 | 199 | 410 |
| 75 | 3.9 | 133 | 259 |
| 76 | 1.7 | 242 | 375 |
| 77 | 4.5 | 154 | 212 |
| 78 | 0.5 | 425 | 565 |
| 79 | 1.9 | 177 | 515 |
| 80 | 1.1 | 334 | 590 |
| 81 | 1.9 | 224 | 396 |
| 82 | 0.5 | 401 | 474 |
| 83 | 0.5 | 352 | 398 |
| 84 | 1.1 | 317 | 555 |
| 85 | 0.7 | 345 | 436 |
| 86 | 2.3 | 147 | 330 |
| 87 | 1.9 | 219 | 297 |
| 88 | 0.7 | 327 | 399 |
| 89 | 4.7 | 153 | 198 |
| 90 | 0.8 | 281 | 317 |
| 91 | 5.6 | 108 | 214 |
| 92 | 0.8 | 324 | 417 |
| 93 | 2.0 | 190 | 422 |
| 94 | 1.1 | 328 | 643 |
| 95 | 3.1 | 130 | 326 |
| 96 | 1.8 | 240 | 395 |
| 97 | 4.2 | 143 | 233 |
| 98 | 2.8 | 239 | 244 |

Experimental Example 2

Measurement of Effect of Inhibiting Cancer Cell Proliferation

HCT116 cells derived from human colorectal cancer were used, and an effect of inhibiting cancer cell proliferation of the biguanide derivative was confirmed by measuring a concentration value (cell growth inhibition concentration, GIC50) at which cell growth was inhibited by 50% using a 3-(4,5-dimethylthiazol-2-yl)-2,5-diphenyltetrazolium bromide (MTT) reagent.

First, HCT116 cells (purchased from the KCLB) were put on a 96-well plate and cultured in a DMEM medium supplemented with 10% fatal bovine serum (commercially available from Gibco Life Technologies (US)) for 16 hours so that approximately 5,000 cells were counted in each well. Subsequently, to obtain the GIC50 value of each compound, the culture media were treated with 100 μM, 25 μM, 6.25 μM, 1.56 μM or 0.39 μM of the compound, and then cultured for 48 hours. In order to determine whether the cells survived after treatment with the compounds, MTT (commercially available from AMRESCO (US)) was added to the culture media which were then cultured for another 3 hours. Formed formazane crystals were dissolved using dimethyl sulfoxide (DMSO) and the absorbance of the resulting solution was measured at 560 nm. After the 48-hour culture, a ratio of a living cell count on a well plate treated with the compounds synthesized in the Examples to a cell count cultured on a well plate not treated with the compound was indicated as cell viability (%) according to the concentration of each treated compound. The cell viability (%) was used to plot a cell viability curve graph and calculate a concentration (GIC50) value of the compound at which the growth was inhibited by 50%, thereby confirming the inhibition effect of cancer cell proliferation. Also, the cell growth inhibitions (%) when the concentration of the treated biguanide derivative and metformin as the control was 100 μM (Examples 4 to 61) is listed in the following Table 3, and the cell growth inhibitions (%) when the concentration of the treated biguanide derivative and metformin as the control was 25 μM (Examples 65 to 98) are listed in the following Table 4.

TABLE 3

| | Effect of inhibition on cancer cell growth | |
|---|---|---|
| Examples | GI50 (μM) | Cell growth inhibition (%) at 100 μM |
| Metformin | 2172 | 6.5 (at 100 μM) |
| 4 | 19.1 | 99.7 |
| 5 | 18.0 | 99.7 |
| 6 | 12.9 | 99.6 |
| 7 | >100 | 19.8 |
| 8 | 42.8 | 99.1 |
| 9 | 28.8 | 99.5 |
| 10 | 8.3 | 97.9 |
| 11 | 3.0 | 98.0 |
| 12 | 84.8 | 53.8 |
| 13 | 77.1 | 57.8 |
| 14 | 17.5 | 98.8 |
| 15 | 10.1 | 99.2 |
| 16 | 10.8 | 99.3 |
| 17 | 13.9 | 99.7 |
| 18 | 2.6 | 99.5 |
| 19 | 9.1 | 99.6 |
| 20 | 54.8 | 93.1 |
| 21 | 10.4 | 99.4 |
| 22 | 18.6 | 37.1 |
| 23 | 89.9 | 29.5 |
| 24 | 33.9 | 99.0 |
| 25 | 4.9 | 96.6 |
| 26 | 8.2 | 96.7 |
| 27 | 33.5 | 96.6 |
| 28 | 8.4 | 100.5 |
| 29 | 9.5 | 100.4 |
| 30 | 7.5 | 99.7 |
| 31 | 7.8 | 99.5 |
| 32 | 7.9 | 99.4 |
| 33 | 3.7 | 99.4 |

TABLE 3-continued

Effect of inhibition on cancer cell growth

| Examples | GI50 (μM) | Cell growth inhibition (%) at 100 μM |
|---|---|---|
| 34 | 6.6 | 99.4 |
| 35 | 18.4 | 99.1 |
| 36 | 11.2 | 99.0 |
| 37 | 135.0 | 45.3 |
| 38 | 108.5 | 47.8 |
| 39 | 123.7 | 39.8 |
| 40 | >100 | 37.4 |
| 41 | 88.2 | 55.9 |
| 42 | >100 | 14.0 |
| 43 | 114.4 | 44.9 |
| 43 | 114.4 | 44.9 |
| 44 | >100 | 27.8 |
| 45 | 107.2 | 47.2 |
| 46 | 12.0 | 100.1 |
| 47 | 10.8 | 100.0 |
| 48 | 42.5 | 97.6 |
| 49 | 57.0 | 91.8 |
| 50 | 116.8 | 46.0 |
| 51 | 102.5 | 48.7 |
| 52 | 15.4 | 100.1 |
| 53 | 43.7 | 97.9 |
| 54 | 14.6 | 98.1 |
| 55 | 22.8 | 97.9 |
| 56 | 26.9 | 97.7 |
| 57 | 26.9 | 97.8 |
| 58 | 7.9 | 98.4 |
| 59 | 141.4 | 44.5 |
| 60 | 99.8 | 50.1 |
| 61 | >100 | 10.5 |

TABLE 4

Effect of inhibition on cancer cell growth

| Examples | GI50 (μM) | Cell growth inhibition (%) at 25 μM |
|---|---|---|
| Metformin | 2172 | 6.5 (at 100 μM) |
| 65 | 18.3 | 66.7 |
| 66 | 18.5 | 67.4 |
| 67 | 9.2 | 100.2 |
| 68 | 45.3 | 29.4 |
| 69 | 1.9 | 100.5 |
| 70 | 3.9 | 100.5 |
| 71 | 5.7 | 100.4 |
| 72 | 8.0 | 100.3 |
| 73 | 6.7 | 100.3 |
| 74 | 8.7 | 100.4 |
| 75 | 9.3 | 100.3 |
| 76 | 5.8 | 100.4 |
| 77 | 11.3 | 100.2 |
| 78 | 7.0 | 100.3 |
| 79 | 9.4 | 98.9 |
| 80 | 6.8 | 99.7 |
| 81 | 7.7 | 100.3 |
| 82 | 7.0 | 100.3 |
| 83 | 6.8 | 100.2 |
| 84 | 10.4 | 97.0 |
| 85 | 7.1 | 100.2 |
| 86 | 27.6 | 49.0 |
| 87 | 10.0 | 100.1 |
| 88 | 6.6 | 100.4 |
| 89 | 6.2 | 100.4 |
| 90 | 3.2 | 100.4 |
| 91 | 11.4 | 100.4 |
| 92 | 7.5 | 100.4 |
| 93 | 3.0 | 100.3 |
| 94 | 2.8 | 100.5 |
| 95 | 2.9 | 100.6 |
| 96 | 10.4 | 100.6 |
| 97 | 9.1 | 100.5 |
| 98 | 45.4 | 28.2 |

The invention claimed is:

1. A compound of following Formula 1 or a pharmaceutically acceptable salt thereof:

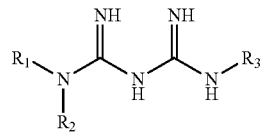

[Formula 1]

wherein $R_1$ and $R_2$ are taken together with nitrogen to which they are attached to form $C_{4-5}$ heterocycloalkene having 5 to 6 ring atoms; and $R_3$ is $C_{1-6}$ alkyl; phenyl; or $C_{1-4}$ alkyl substituted with phenyl, wherein the $C_{4-5}$ heterocycloalkene is unsubstituted or substituted with at least one substituent selected from the group consisting of halogen, hydroxy and $C_{1-6}$ alkyl, the phenyl is unsubstituted or substituted with at least one non-hydrogen substituent selected from the group consisting of halogen, hydroxy, $C_{1-6}$ alkyl, $C_{1-6}$ alkoxy, $C_{1-6}$ haloalkyl, and $C_{1-6}$ haloalkoxy.

2. The compound of Formula 1 or the pharmaceutically acceptable salt thereof of claim 1, wherein $R_1$ and $R_2$ are taken together with nitrogen to which they are attached to form $C_{4-5}$ heterocycloalkene having 5 to 6 ring atoms; and $R_3$ is $C_{1-6}$ alkyl; phenyl; or $C_{1-2}$ alkyl substituted with phenyl, wherein the $C_{4-5}$ heterocycloalkene is unsubstituted or substituted with $C_{1-6}$ alkyl, and the phenyl is unsubstituted or substituted with at least one non-hydrogen substituent selected from the group consisting of halogen, hydroxy, $C_{1-6}$ alkyl, $C_{1-6}$ alkoxy, $C_{1-6}$ haloalkyl, and $C_{1-6}$ haloalkoxy.

3. The compound of Formula 1 or the pharmaceutically acceptable salt thereof of claim 1, wherein $R_1$ and $R_2$ are taken together with nitrogen to which they are attached to form $C_{4-5}$ heterocycloalkene having 5 to 6 ring atoms; and $R_3$ is $C_{1-6}$ alkyl; phenyl; or $C_{1-2}$ alkyl substituted with phenyl, wherein the $C_{4-5}$ heterocycloalkene is unsubstituted or substituted with $C_{1-2}$ alkyl, and the phenyl is unsubstituted or substituted with at least one non-hydrogen substituent selected from the group consisting of halogen, $C_{1-2}$ alkoxy, $C_{1-2}$ haloalkyl, and $C_{1-2}$ haloalkoxy.

4. The compound of Formula 1 or the pharmaceutically acceptable salt thereof of claim 1, wherein $R_1$ and $R_2$ are taken together with nitrogen to which they are attached to form $C_{4-5}$ heterocycloalkene selected from the group consisting of dihydropyrrolinyl; dihydropyridinyl; and tetrahydropyridinyl; and $R_3$ is $C_{1-6}$ alkyl; phenyl; or $C_{1-4}$ alkyl substituted with phenyl, wherein the $C_{4-5}$ heterocycloalkene is unsubstituted or substituted with $C_{1-6}$ alkyl, and the phenyl is unsubstituted or substituted with at least one non-hydrogen substituent selected from the group consisting of halogen, hydroxy, $C_{1-6}$ alkyl, $C_{1-6}$ alkoxy, $C_{1-6}$ haloalkyl, and $C_{1-6}$ haloalkoxy.

5. The compound of Formula 1 or the pharmaceutically acceptable salt thereof of claim 1,
wherein $R_1$ and $R_2$ are taken together with nitrogen to which they are attached to form dihydropyrrolinyl or tetrahydropyridinyl which is unsubstituted or substituted with $C_{1-4}$ alkyl; and
$R_3$ is $C_{1-6}$ alkyl; phenyl; or $C_{1-4}$ alkyl substituted with phenyl,
wherein the phenyl is unsubstituted or substituted with at least one non-hydrogen substituent selected from the group consisting of halogen, $C_{1-4}$ alkoxy, $C_{1-4}$ haloalkyl, and $C_{1-4}$ haloalkoxy.

6. The compound of Formula 1 or the pharmaceutically acceptable salt thereof of claim 1,
wherein $R_1$ and $R_2$ are taken together with nitrogen to which they are attached to form dihydropyrrolinyl or tetrahydropyridinyl which is unsubstituted or substituted with $C_{1-2}$ alkyl; and
$R_3$ is $C_{3-6}$ alkyl; phenyl; or $C_{1-2}$ alkyl substituted with phenyl,
wherein the phenyl is unsubstituted or substituted with at least one non-hydrogen substituent selected from the group consisting of halogen, $C_{1-2}$ alkoxy, $C_{1-2}$ haloalkyl, and $C_{1-2}$ haloalkoxy.

7. The compound of Formula 1 or the pharmaceutically acceptable salt thereof of claim 1,
wherein $R_1$ and $R_2$ are taken together with nitrogen to which they are attached to form dihydropyrrolinyl or tetrahydropyridinyl which is unsubstituted or substituted with methyl; and
$R_3$ is butyl; propyl; hexyl; phenyl; or methyl substituted with phenyl,
and
the phenyl is unsubstituted or substituted with at least one non-hydrogen substituent selected from the group consisting of halogen, methoxy, trihalomethyl, and trihalomethoxy.

8. The compound of Formula 1 or the pharmaceutically acceptable salt thereof of claim 1, wherein the compound of Formula 1 is
N1-1,2-dihydropyrrole-N5-(4-trifluoromethoxy)phenyl biguanide;
N1-1,2-dihydropyrrole-N5-(4-trifluoromethyl)phenyl biguanide;
N1-1,2-dihydropyrrole-N5-(3-trifluoromethyl)phenyl biguanide;
N1-1,2-dihydropyrrole-N5-(4-fluoro)phenyl biguanide;
N1-1,2-dihydropyrrole-N5-(4-chloro)phenyl biguanide;
N1-1,2-dihydropyrrole-N5-(4-bromo)phenyl biguanide;
N1-1,2-dihydropyrrole-N5-(3-chloro, 4-trifluoromethoxy)phenyl biguanide;
N1-1,2,3,6-tetrahydropyridine-N5-(3-chloro, 4-trifluoromethoxy)phenyl biguanide;
N1-1,2-dihydropyrrole-N5-(3-trifluoromethyl)benzyl biguanide;
N1-1,2-dihydropyrrole-N5-(4-trifluoromethyl)benzyl biguanide;
N1-1,2-dihydropyrrole-N5-(3-trifluoromethoxy)benzyl biguanide;
N1-(3-methyl)-1,2-dihydropyrrole-N5-(4-trifluoromethoxy)phenyl biguanide;
N1-(3-methyl)-1,2-dihydropyrrole-N5-(4-trifluoromethyl)phenyl biguanide;
N1-(3-methyl)-1,2-dihydropyrrole-N5-(4-chloro)phenyl biguanide;
N1-(3-methyl)-1,2-dihydropyrrole-N5-(4-chloro, 3-trifluoromethyl)phenyl biguanide;
N1-(3-methyl)-1,2-dihydropyrrole-N5-(3-trifluoromethyl)phenyl biguanide;
N1-(3-methyl)-1,2-dihydropyrrole-N5-(4-fluoro)phenyl biguanide;
N1-(3-methyl)-1,2-dihydropyrrole-N5-(4-bromo)phenyl biguanide;
N1-(3-methyl)-1,2-dihydropyrrole-N5-(4-methoxy)phenyl biguanide;
N1-(3-methyl)-1,2-dihydropyrrole-N5-(3,4-dimethoxy)phenyl biguanide;
N1-(3-methyl)-1,2-dihydropyrrole-N5-(4-trifluoromethoxy)benzyl biguanide;
N1-(3-methyl)-1,2-dihydropyrrole-N5-(3-trifluoromethoxy)phenyl biguanide;
N1-(3-methyl)-1,2-dihydropyrrole-N5-(4-trifluoromethyl)benzyl biguanide;
N1-(3-methyl)-1,2-dihydropyrrole-N5-(4-chloro, 3-trifluoromethyl)benzyl biguanide;
N1-1,2,3,6-tetrahydropyridine-N5-(4-trifluoromethoxy)phenyl biguanide;
N1-1,2,3,6-tetrahydropyridine-N5-(4-trifluoromethyl)phenyl biguanide;
N1-1,2,3,6-tetrahydropyridine-N5-(3-trifluoromethoxy)phenyl biguanide;
N1-1,2,3,6-tetrahydropyridine-N5-(3-trifluoromethyl)phenyl biguanide;
N1-1,2,3,6-tetrahydropyridine-N5-(4-fluoro, 3-trifluoromethyl)phenyl biguanide;
N1-1,2,3,6-tetrahydropyridine-N5-(4-chloro, 3-trifluoromethoxy)phenyl biguanide;
N1-1,2,3,6-tetrahydropyridine-N5-(3-fluoro,4-trifluoromethoxy)phenyl biguanide;
N1-1,2,3,6-tetrahydropyridine-N5-(4-chloro)phenyl biguanide;
N1-1,2,3,6-tetrahydropyridine-N5-(4-bromo)phenyl biguanide;
N1-1,2,3,6-tetrahydropyridine-N5-(4-fluoro)phenyl biguanide;
N1-1,2,3,6-tetrahydropyridine-N5-(3,5-dimethoxy)phenyl biguanide;
N1-1,2,3,6-tetrahydropyridine-N5-phenyl biguanide;
N1-1,2,3,6-tetrahydropyridine-N5-(4-methoxy)phenyl biguanide;
N1-1,2,3,6-tetrahydropyridine-N5-(3-methoxy)phenyl biguanide;
N1-1,2-dihydropyrrole-N5-(4-methoxy)phenyl biguanide;
N1-1,2-dihydropyrrole-N5-(3-methoxy)phenyl biguanide;
N1-1,2-dihydropyrrole-N5-phenyl biguanide;
N1-1,2-dihydropyrrole-N5-(3,5-dimethoxy)phenyl biguanide;
N1-1,2-dihydropyrrole-N5-(4-fluoro, 3-trifluoromethyl)phenyl biguanide;
N1-1,2-dihydropyrrole-N5-(3-fluoro, 4-trifluoromethyl)phenyl biguanide;
N1-1,2,3,6-tetrahydropyridine-N5-(4-methyl)phenyl biguanide;
N1-1,2,3,6-tetrahydropyridine-N5-(3-methyl)phenyl biguanide;
N1-1,2-dihydropyrrole-N5-(4-methyl)phenyl biguanide;
N1-1,2-dihydropyrrole-N5-(3-methyl)phenyl biguanide;

N1-1,2-dihydropyrrole-N5-(3-trifluoromethoxy)phenyl biguanide;
N1-1,2,3,6-tetrahydropyridine-N5-hexyl biguanide;
N1-1,2,3,6-tetrahydropyridine-N5-(4-trifluoromethoxy) benzyl biguanide;
N1-1,2,3,6-tetrahydropyridine-N5-(3-trifluoromethoxy) benzyl biguanide;
N1-1,2,3,6-tetrahydropyridine-N5-(4-trifluoromethyl) benzyl biguanide;
N1-1,2,3,6-tetrahydropyridine-N5-(3-trifluoromethyl) benzyl biguanide;
N1-1,2,3,6-tetrahydropyridine-N5-(4-chloro, 3-trifluoromethyl)benzyl biguanide;
N1-1,2,3,6-tetrahydropyridine-N5-butyl biguanide; and
N1-1,2,3,6-tetrahydropyridine-N5-propyl biguanide.

9. The compound of Formula 1 or the pharmaceutically acceptable salt thereof of claim 1,
wherein the pharmaceutically acceptable salt is a salt with an acid selected from the group consisting of formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, benzensulfonic acid, p-toluenesulfonic acid, methanesulfonic acid, dichloroacetic acid, aminooxy acetic acid, hydrochloric acid, hydrobromic acid, sulfuric acid, phosphoric acid, nitric acid, carbonic acid, and boric acid.

10. A method of preparing a compound of following Formula 1, comprising:
reacting a compound of the following Formula 2 with a dicyanamide in an organic solvent to obtain a compound of the following Formula 3; and
reacting the compound of the following Formula 3 with a compound of Formula 4 in an organic solvent to obtain the compound of the following Formula 1:

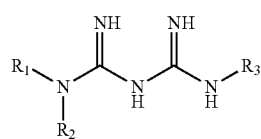

[Formula 1]

[Formula 2]

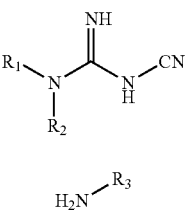

[Formula 3]

[Formula 4]

wherein $R_1$ and $R_2$ are taken together with nitrogen to which they are attached to form $C_{4-5}$ heterocycloalkene having 5 to 6 ring atoms; and $R_3$ is $C_{1-6}$ alkyl; phenyl; or $C_{1-4}$ alkyl substituted with phenyl, wherein the $C_{4-5}$ heterocycloalkene is unsubstituted or substituted with at least one substituent selected from the group consisting of halogen, hydroxyl, and $C_{1-6}$ alkyl, the phenyl is unsubstituted or substituted with at least one non-hydrogen substituent selected from the group consisting of halogen, hydroxy, $C_{1-6}$ alkyl, $C_{1-6}$ alkoxy, $C_{1-6}$ haloalkyl, and $C_{1-6}$ haloalkoxy.

11. A method of treating a cancer, comprising:
administering a therapeutically effective amount of the compound of Formula 1 or the pharmaceutically acceptable salt thereof defined in claim 1 to a subject, wherein the cancer is selected from the group consisting of uterine cancer, breast cancer, gastric cancer, brain cancer, rectal cancer, colorectal cancer, lung cancer, skin cancer, blood cancer, pancreatic cancer, prostate cancer, and liver cancer.

12. The method of claim 11, wherein the method inhibits metastasis of the cancer.

* * * * *

UNITED STATES PATENT AND TRADEMARK OFFICE
CERTIFICATE OF CORRECTION

PATENT NO. : 9,884,821 B2
APPLICATION NO. : 14/766203
DATED : February 6, 2018
INVENTOR(S) : Chang Hee Min et al.

It is certified that error appears in the above-identified patent and that said Letters Patent is hereby corrected as shown below:

In the Specification

Column 6, Line 22, replace "(4-methoxyl)" with --(4-methoxy)--;
　　Line 57, replace "(4-methoxyl)" with --(4-methoxy)--;
　　Line 59, replace "(3-methoxyl)" with --(3-methoxy)--;
　　Line 61, replace "(4-methoxyl)" with --(4-methoxy)--;
　　Line 62, replace "(3-methoxyl)" with --(3-methoxy)--.

Column 8, Line 33, replace "benzensulfonic acid" with --benzenesulfonic acid--;
　　Line 54, replace "benzensulfonic acid" with --benzenesulfonic acid--.

Column 19, Line 4, replace "(4-methoxyl)" with --(4-methoxy)--;

Line 60, replace " 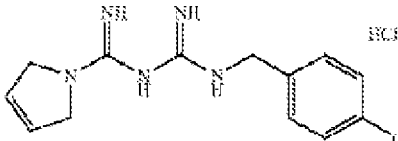 " with 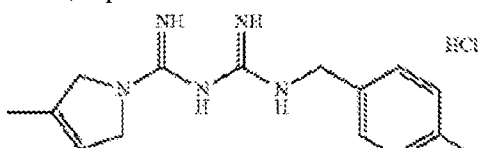 --.

Column 24, Line 51, replace "(4-methoxyl)" with --(4-methoxy)--.

Column 25, Line 3, replace "(3-methoxyl)" with --(3-methoxy)--;
　　Line 21, replace "(4-methoxyl)" with --(4-methoxy)--;
　　Line 38, replace "(3-methoxyl)" with --(3-methoxy)--.

Column 40, Line 18, replace "7.48 t, 1H)," with --(7.48 t, 1H)--.

Signed and Sealed this
Third Day of July, 2018

Andrei Iancu
*Director of the United States Patent and Trademark Office*

In the Claims

Column 51, Line 25, replace "benzensulfonic acid" with --benzenesulfonic acid--.

Column 52, Line 31, replace "hydroxy" with --hydroxyl--.